(12) United States Patent
Davies et al.

(10) Patent No.: US 9,320,862 B2
(45) Date of Patent: *Apr. 26, 2016

(54) FLUID DISPENSING DEVICE

(71) Applicant: Glaxo Group Limited, Brentford, Middlesex (GB)

(72) Inventors: Michael Birsha Davies, Hertfordshire (GB); Mark Graham Hedley, Hertfordshire (GB); James William Godfrey, Hertfordshire (GB)

(73) Assignee: Glaxo Group Limited, Brentford, Middlesex (GB)

( * ) Notice: Subject to any disclaimer, the term of this patent is extended or adjusted under 35 U.S.C. 154(b) by 4 days.

This patent is subject to a terminal disclaimer.

(21) Appl. No.: 14/303,773

(22) Filed: Jun. 13, 2014

(65) Prior Publication Data

US 2014/0290652 A1 Oct. 2, 2014

Related U.S. Application Data

(63) Continuation of application No. 10/577,977, filed as application No. PCT/GB2004/004626 on Nov. 2, 2004, now Pat. No. 8,752,543.

(30) Foreign Application Priority Data

Nov. 3, 2003 (GB) .................................. 0325629.4
Mar. 11, 2004 (GB) .................................. 0405477.1
Sep. 17, 2004 (GB) .................................. 0420539.9

(51) Int. Cl.
*A61M 15/00* (2006.01)
*A61M 15/08* (2006.01)
(Continued)

(52) U.S. Cl.
CPC ......... *A61M 15/0001* (2014.02); *A61M 15/009* (2013.01); *A61M 15/08* (2013.01); *B05B11/3052* (2013.01); *B05B 11/3056* (2013.01); *B05B 11/3059* (2013.01); *B65D 83/386* (2013.01); *B05B 11/0037* (2013.01); *B65D 83/16* (2013.01); *B65D 83/201* (2013.01)

(58) Field of Classification Search
CPC . A61M 11/00; A61M 11/006; A61M 11/008; A61M 11/08; A61M 15/00; A61M 15/0001; A61M 15/009; B65D 83/14; B65D 83/16; B65D 83/20; B65D 83/201; B65D 83/202; B65D 83/206; B65D 83/207; B65D 2251/1066; B65D 2251/1075; B65D 2543/00888; B65D 43/26; B65D 43/265; B65D 43/267; B65D 47/249; B65D 47/248; B65D 47/20
USPC ..................................................... 128/200.14
See application file for complete search history.

(56) References Cited

U.S. PATENT DOCUMENTS 2,602,569 A 7/1952 Ryan
2,673,008 A 3/1954 Ryan
(Continued)

FOREIGN PATENT DOCUMENTS

DE 2633901 A1 2/1977
DE 19610456 A1 9/1997
(Continued)

OTHER PUBLICATIONS

U.S. Appl. No. 10/513,201, filed May 7, 2003.
(Continued)

*Primary Examiner* — Justine Yu
*Assistant Examiner* — Colin W Stuart
(74) *Attorney, Agent, or Firm* — James P. Riek

(57) ABSTRACT

A fluid dispensing device for dispensing a fluid form medicament formulation having a viscosity of from 10 to 2000 mPa·s, is disclosed having a housing and a fluid discharge device. The fluid discharge device is arranged to be actuated by one or more levers, so as to apply a force to the fluid discharge device which is used to move a container forming part of the fluid discharge device, along a longitudinal axis of the fluid discharge device to cause actuation of a pump forming. A pre-load mechanism prevents actuation of the pump until a pre-determined force is applied to each lever of sufficient magnitude to guarantee the production of a well-developed, efficient spray from the fluid dispensing device.

18 Claims, 22 Drawing Sheets

(51) Int. Cl.
  *B65D 83/38*  (2006.01)
  *B65D 83/16*  (2006.01)
  *B65D 83/20*  (2006.01)
  *B05B 11/00*  (2006.01)

(56) References Cited

U.S. PATENT DOCUMENTS

| | | | |
|---|---|---|---|
| 2,904,223 | A | 9/1959 | Ryan |
| 3,237,809 | A | 3/1966 | Daragan et al. |
| 3,272,391 | A | 9/1966 | Meshberg |
| 3,405,843 | A | 10/1968 | Watson, Jr. |
| 3,516,424 | A | 6/1970 | Eagle |
| 4,083,476 | A | 4/1978 | Schwartz et al. |
| 4,111,338 | A | 9/1978 | Cheng et al. |
| 4,132,359 | A | 1/1979 | Nozawa |
| 4,155,487 | A | 5/1979 | Blake |
| 4,185,776 | A | 1/1980 | Nozawa |
| 4,223,812 | A | 9/1980 | van Lit |
| 4,402,430 | A | 9/1983 | Fox et al. |
| 4,648,393 | A | 3/1987 | Landis et al. |
| 4,678,106 | A | 7/1987 | Newell et al. |
| 4,765,515 | A | 8/1988 | Lippman |
| 4,771,769 | A | 9/1988 | Hegemann et al. |
| 4,807,786 | A | 2/1989 | Gueret |
| 4,860,738 | A | 8/1989 | Hegemann et al. |
| 4,921,142 | A | 5/1990 | Graf et al. |
| 4,944,429 | A | 7/1990 | Bishop et al. |
| 4,946,069 | A | 8/1990 | Fuchs |
| 5,062,549 | A | 11/1991 | Smith et al. |
| 5,190,029 | A | 3/1993 | Byron et al. |
| 5,273,189 | A | 12/1993 | Jouillat et al. |
| 5,487,489 | A | 1/1996 | Weiss et al. |
| 5,568,884 | A | 10/1996 | Bruna |
| 5,899,365 | A | 5/1999 | Eichler et al. |
| 6,152,330 | A | 11/2000 | Polan |
| 6,189,739 | B1 | 2/2001 | Von Schuckmann |
| 6,237,812 | B1 | 5/2001 | Fukada |
| 6,257,457 | B1 | 7/2001 | Oechsel |
| 6,261,274 | B1 | 7/2001 | Arghyris et al. |
| 6,302,101 | B1 | 10/2001 | Py |
| 6,305,371 | B1 | 10/2001 | Frid et al. |
| 6,315,165 | B1 | 11/2001 | Regan |
| 6,338,422 | B1 | 1/2002 | DeJonge |
| 6,364,166 | B1 | 4/2002 | Ritsche et al. |
| 6,382,205 | B1 | 5/2002 | Weinstein et al. |
| 6,382,465 | B1 | 5/2002 | Greiner-Perth |
| 6,419,124 | B1 | 7/2002 | Hennemann et al. |
| 6,484,715 | B1 | 11/2002 | Ritsche et al. |
| 6,527,144 | B2 | 3/2003 | Ritsche et al. |
| 6,568,389 | B1 | 5/2003 | Rand et al. |
| 6,578,741 | B2 | 6/2003 | Ritsche et al. |
| 6,644,305 | B2 | 11/2003 | MacRae et al. |
| 6,745,760 | B2 | 6/2004 | Grychowski et al. |
| 6,750,210 | B2 | 6/2004 | Biggadike |
| 6,860,411 | B2 | 3/2005 | Stradella |
| 7,108,159 | B2 | 9/2006 | Stradella |
| 7,353,971 | B2 | 4/2008 | Stradella |
| 8,062,264 | B2 | 11/2011 | Godfrey et al. |
| 8,752,543 | B2 * | 6/2014 | Davies et al. ............ 128/200.14 |
| 2001/0013343 | A1 | 8/2001 | Andersson |
| 2002/0008122 | A1 | 1/2002 | Ritsche et al. |
| 2002/0011530 | A1 | 1/2002 | Fuchs |
| 2002/0117513 | A1 | 8/2002 | Helmlinger |
| 2002/0170923 | A1 | 11/2002 | Vatman |
| 2002/0170928 | A1 | 11/2002 | Grychowski et al. |
| 2002/0173496 | A1 | 11/2002 | Biggadike |
| 2003/0052196 | A1 | 3/2003 | Fuchs |
| 2003/0100867 | A1 | 5/2003 | Fuchs |
| 2004/0182814 | A1 | 9/2004 | Suffa |
| 2004/0245291 | A1 | 12/2004 | Simon et al. |
| 2005/0040188 | A1 | 2/2005 | Herry et al. |
| 2005/0072861 | A1 | 4/2005 | Petit |
| 2005/0076861 | A1 | 4/2005 | Matsuo |
| 2005/0098175 | A1 | 5/2005 | Stradella |
| 2005/0211241 | A1 | 9/2005 | Anderson et al. |
| 2005/0224525 | A1 | 10/2005 | Davies |
| 2005/0234402 | A1 | 10/2005 | Collins et al. |
| 2005/0258191 | A1 | 11/2005 | Davies |
| 2006/0108378 | A1 | 5/2006 | Cohen et al. |
| 2006/0191959 | A1 | 8/2006 | Davies et al. |
| 2007/0056585 | A1 | 3/2007 | Davies et al. |
| 2007/0095853 | A1 | 5/2007 | Bonney et al. |
| 2007/0131717 | A1 | 6/2007 | Davies et al. |
| 2007/0138207 | A1 | 6/2007 | Bonney et al. |
| 2008/0249459 | A1 | 10/2008 | Godfrey et al. |

FOREIGN PATENT DOCUMENTS

| | | |
|---|---|---|
| EP | 0412524 | 2/1991 |
| EP | 0461277 B1 | 12/1991 |
| EP | 1129786 A2 | 9/2001 |
| EP | 1281443 A2 | 5/2003 |
| FR | 1444387 | 7/1966 |
| FR | 2570000 | 3/1986 |
| FR | 2671294 | 7/1992 |
| FR | 2807954 | 10/2001 |
| FR | 2812826 | 2/2002 |
| FR | 2830519 | 4/2003 |
| GB | 173123 | 12/1921 |
| GB | 659132 | 10/1951 |
| GB | 906837 | 9/1962 |
| GB | 1097254 | 1/1968 |
| GB | 1481199 | 7/1977 |
| GB | 2251898 | 7/1992 |
| JP | H-03198866 | 8/1991 |
| JP | 04057264 | 2/1992 |
| JP | H-08508694 | 9/1996 |
| JP | H-09048455 | 2/1997 |
| JP | 09225363 | 9/1997 |
| JP | H-09313998 | 12/1997 |
| JP | H-10001155 | 1/1998 |
| JP | 10179739 | 7/1998 |
| JP | 2000511499 | 9/2000 |
| JP | 2000355382 | 12/2000 |
| WO | WO-9405593 A1 | 3/1994 |
| WO | WO-9411115 A1 | 5/1994 |
| WO | WO-9901229 A1 | 1/1999 |
| WO | WO-9938555 A1 | 8/1999 |
| WO | WO-9949984 A1 | 10/1999 |
| WO | WO-0007740 A1 | 2/2000 |
| WO | WO-0018458 A1 | 4/2000 |
| WO | WO-0136018 A2 | 5/2001 |
| WO | WO-0220168 A1 | 3/2002 |
| WO | WO-0220370 A1 | 3/2002 |
| WO | WO-0244056 A1 | 6/2002 |
| WO | WO-0249698 A1 | 6/2002 |
| WO | WO-02053294 A1 | 7/2002 |
| WO | WO-03020350 A1 | 3/2003 |
| WO | WO-03026803 A1 | 4/2003 |
| WO | WO-03026804 A1 | 4/2003 |
| WO | WO-03026805 A1 | 4/2003 |
| WO | WO-03029105 A1 | 4/2003 |
| WO | WO-03041865 A1 | 5/2003 |
| WO | WO-03043909 A2 | 5/2003 |
| WO | WO-03061843 A1 | 7/2003 |
| WO | WO-03095006 A2 | 11/2003 |
| WO | WO-03095007 A2 | 11/2003 |
| WO | WO-2004013009 A1 | 2/2004 |
| WO | WO-2004080606 A1 | 9/2004 |
| WO | WO-2004012799 A2 | 12/2004 |
| WO | WO-2005028007 A1 | 3/2005 |
| WO | WO-2005044354 A1 | 5/2005 |
| WO | WO-2005087615 A1 | 9/2005 |
| WO | WO-2006109021 A1 | 10/2006 |

OTHER PUBLICATIONS

Non-Final Rejection issued Aug. 18, 2008 for U.S. Appl. No. 10/513,201.

Amendment filed Feb. 18, 2009 in response to Non-Final Rejection issued Aug. 18, 2008 for U.S. Appl. No. 10/513,201.

Final Rejection issued May 27, 2009 for U.S. Appl. No. 10/513,201.

(56) References Cited

OTHER PUBLICATIONS

Request for Continued Eamination (RCE) with Amendment and Terminal Disclaimer filed Aug. 27, 2009 for U.S. Appl. No. 10/513,201.
Terminal Disclaimer approved by USPTO on Sep. 27, 2009 for U.S. Appl. No. 10/513,201.
Non-Final Rejection issued Mar. 18, 2010 for U.S. Appl. No. 10/513,201.
Amendment filed Jun. 17, 2010 in response to Non-Final Rejection issued Mar. 18, 2010 for U.S. Appl. No. 10/513,201.
Notice of Allowance issued Sep. 1, 2010 for U.S. Appl. No. 10/513,201.
Request for Continued Eamination (RCE) with Amendment and IDS filed Dec. 1, 2010 for U.S. Appl. No. 10/513,201.
Notice of Allowance issued Dec. 17, 2010 for U.S. Appl. No. 10/513,201.
Request for Continued Eamination (RCE) with IDS filed Mar. 17, 2011 for U.S. Appl. No. 10/513,201.
Notice of Allowance issued Apr. 4, 2011 for U.S. Appl. No. 10/513,201.
Request for Continued Eamination (RCE) with IDS filed Jun. 16, 2011 for U.S. Appl. No. 10/513,201.
Notice of Allowance issued Jul. 12, 2011 for U.S. Appl. No. 10/513,201.
Request for Continued Eamination (RCE) with IDS filed Oct. 17, 2011 for U.S. Appl. No. 10/513,201.
Notice of Allowance issued Aug. 27, 2012 for U.S. Appl. No. 10/513,201.
Amendment after Allowance filed Dec. 7, 2012 for U.S. Appl. No. 10/513,201.
U.S. Appl. No. 10/523,163, filed Jan. 27, 2005.
Non-Final Rejection issued Jun. 25, 2007 for U.S. Appl. No. 10/523,163.
Amendment filed Dec. 20, 2007 in response to Non-Final Rejection issued Jun. 25, 2007 for U.S. Appl. No. 10/523,163.
Notice of Allowance issued Feb. 8, 2008 for U.S. Appl. No. 10/523,163.
Examiner Interview Summary Record issued Feb. 8, 2008 for U.S. Appl. No. 10/523,163.
Request for Continued Eamination (RCE) with IDS filed May 8, 2008 for U.S. Appl. No. 10/523,163.
Notice of Allowance issued Jul. 28, 2008 for U.S. Appl. No. 10/523,163.
Request for Continued Eamination (RCE) with IDS filed Oct. 28, 2008 for U.S. Appl. No. 10/523,163.
Non-Final Rejection issued Nov. 17, 2008 for U.S. Appl. No. 10/523,163.
Amendment filed May 12, 2009 in response to Non-Final Rejection issued Nov. 17, 2008 for U.S. Appl. No. 10/523,163.
Final Rejection issued May 29, 2009 for U.S. Appl. No. 10/523,163.
U.S. Appl. No. 10/548,716 filed Sep. 8, 2005.
Restriction Requirement issued Jan. 26, 2009 for U.S. Appl. No. 10/548,716.
Response filed Feb. 19, 2009 in reply to Restriction Requirement issued Jan. 26, 2009 for U.S. Appl. No. 10/548,716.
Non-Final Rejection issued May 20, 2009 for U.S. Appl. No. 10/548,716.
Amendment filed Aug. 20, 2009 in response to Non-Final Rejection issued May 20, 2009 for U.S. Appl. No. 10/548,716.
Non-Final Rejection issued Nov. 27, 2009 for U.S. Appl. No. 10/548,716.
Amendment filed Mar. 1, 2010 in response to Non-Final Rejection issued Nov. 27, 2009 for U.S. Appl. No. 10/548,716.
Notice of Allowance issued Apr. 6, 2010 for U.S. Appl. No. 10/548,716.
Request for Continued Examination (RCE) with IDS filed Jul. 6, 2010 for U.S. Appl. No. 10/548,716.
Notice of Allowance issued Aug. 12, 2010 for U.S. Appl. No. 10/548,716.
U.S. Appl. No. 10/598,464, filed Mar. 10, 2005.
Non-Final Rejection issued Aug. 6, 2009 for U.S. Appl. No. 10/598,464.
Amendment filed Nov. 3, 2009 in response to Non-Final Rejection issued Aug. 6, 2009 for U.S. Appl. No. 10/598,464.
Non-Final Rejection issued Mar. 1, 2010 for U.S. Appl. No. 10/598,464.
Amendment filed Jun. 1, 2010 in response to Non-Final Rejection issued Mar. 1, 2010 for U.S. Appl. No. 10/598,464.
Non-Final Rejection issued Sep. 3, 2010 for U.S. Appl. No. 10/598,464.
Amendment filed Dec. 14, 2010 in response to Non-Final Rejection issued Sep. 3, 2010 for U.S. Appl. No. 10/598,464.
Ex Parte Quayle Action issued Jan. 25, 2011 for U.S. Appl. No. 10/598,464.
Response to Ex Parte Quayle Action filed Mar. 25, 2011 for U.S. Appl. No. 10/598,464.
Notice of Allowance issued May 26, 2011 for U.S. Appl. No. 10/598,464.
Request for Continued Examination (RCE) with IDS filed Jul. 14, 2011 for U.S. Appl. No. 10/598,464.
Notice of Allowance issued Aug. 8, 2011 for U.S. Appl. No. 10/598,464.
Request for Continued Examination (RCE) with IDS filed Nov. 7, 2011 for U.S. Appl. No. 10/598,464.
Notice of Allowance issued Nov. 28, 2011 for U.S. Appl. No. 10/598,464.
U.S. Appl. No. 10/572,916, filed Nov. 1, 2006.
Restriction Requirement issued Jun. 24, 2010 for U.S. Appl. No. 10/572,916.
U.S. Appl. No. 10/577,977, filed May 3, 2006.
Non-Final Office Action issued Sep. 18, 2009 for U.S. Appl. No. 10/577,977.
Amendment filed Jan. 18, 2010 in response to Non-Final Office Action issued Sep. 18, 2009 for U.S. Appl. No. 10/577,977.
Notice of Allowance issued Apr. 21, 2010 for U.S. Appl. No. 10/577,977.
Request for Continued Examination (RCE) with Amendment and IDS filed Jul. 19, 2010 for U.S. Appl. No. 10/577,977.
Notice of Allowance issued Aug. 6, 2010 for U.S. Appl. No. 10/577,977.
Request for Continued Examination (RCE) with Amendment and IDS filed Nov. 8, 2010 for U.S. Appl. No. 10/577,977.
Non-Final Office Action issued Jun. 17, 2013 for U.S. Appl. No. 10/577,977.
Amendment and Terminal Disclaimer filed Sep. 16, 2013 in response to Non-Final Office Action dated Jun. 17, 2013 for U.S. Appl. No. 10/577,977.
Terminal Disclaimer approved by USPTO on Sep. 18, 2013 for U.S. Appl. No. 10/577,977.
Terminal Disclaimer filed Sep. 26, 2013 for U.S. Appl. No. 10/577,977.
Terminal Disclaimer approved by USPTO on Oct. 3, 2013 for U.S. Appl. No. 10/577,977.
Notice of Allowance issued Oct. 17, 2013 for U.S. Appl. No. 10/577,977.
Amendment after Allowance filed Jan. 15, 2014 for U.S. Appl. No. 10/577,977.
Supplemental Amendment after Allowance filed Jan. 16, 2014 for U.S. Appl. No. 10/577,977.
U.S. Appl. No. 11/911,060, filed May 27, 2008.
Non-Final Office Action dated Sep. 8, 2008 for U.S. Appl. No. 11/911,060.
Amendment filed Mar. 9, 2009 in response to Non-Final Office Action dated Sep. 8, 2008 for U.S. Appl. No. 11/911,060.
Final Office Action dated May 14, 2009 for U.S. Appl. No. 11/911,060.
Request for Continued Examination (RCE) with Amendment and IDS filed Jul. 15, 2009 for U.S. Appl. No. 11/911,060.
Non-Final Office Action issued Aug. 7, 2009 for U.S. Appl. No. 11/911,060.

(56) References Cited

OTHER PUBLICATIONS

Amendment filed Feb. 4, 2010 in response to Non-Final Office Action issued Aug. 7, 2009 for U.S. Appl. No. 11/911,060.
Final Office Action dated May 13, 2010 for U.S. Appl. No. 11/911,060.
Request for Continued Examination (RCE) with Amendment and Terminal Disclaimer filed Jul. 13, 2010 in response to Final Office Action dated May 13, 2010 for U.S. Appl. No. 11/911,060.
Terminal Disclaimer approved by USPTO on Aug. 10, 2010 for U.S. Appl. No. 11/911,060.
Notice of Allowance issued Mar. 9, 2011 for U.S. Appl. No. 11/911,060.
Request for Continued Examination (RCE) with IDS filed Jun. 6, 2011 for U.S. Appl. No. 11/911,060.
Notice of Allowance issued Jun. 30, 2011 for U.S. Appl. No. 11/911,060.

* cited by examiner

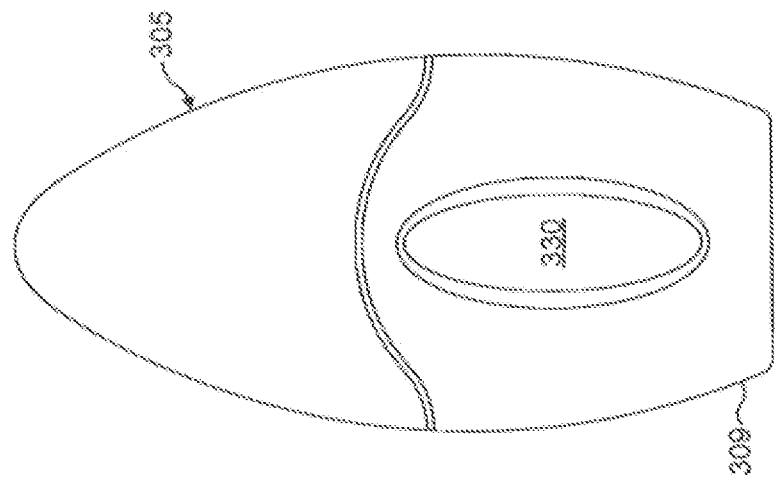
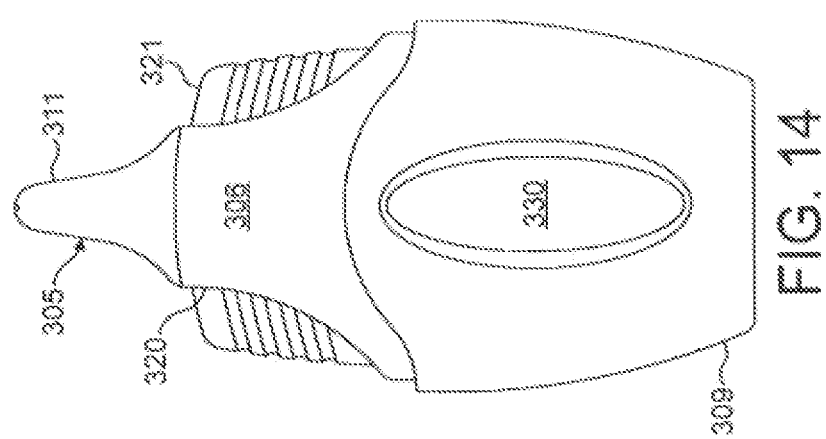

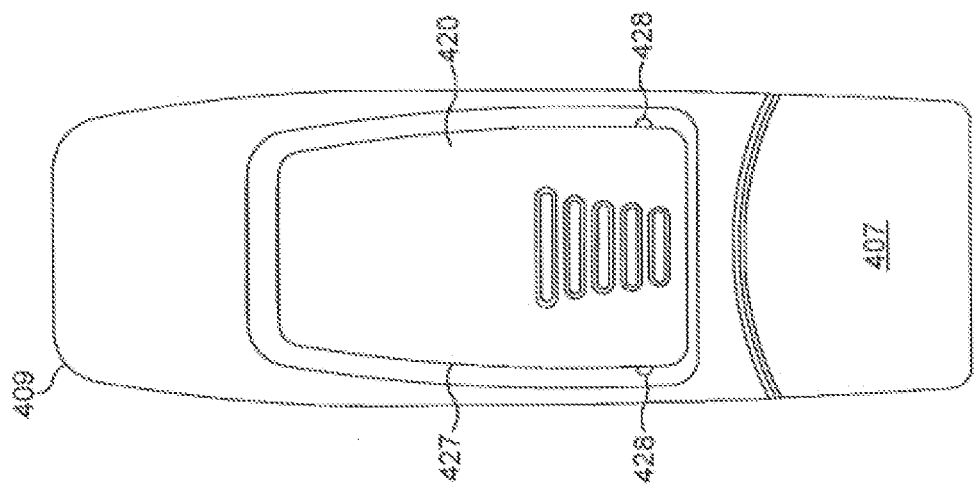
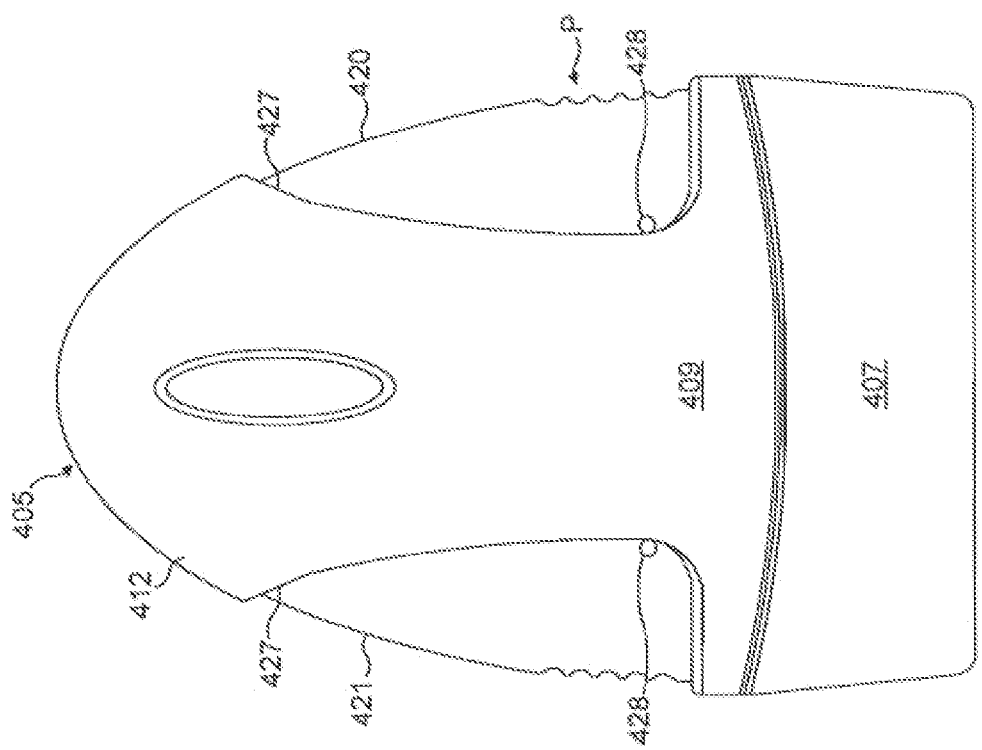

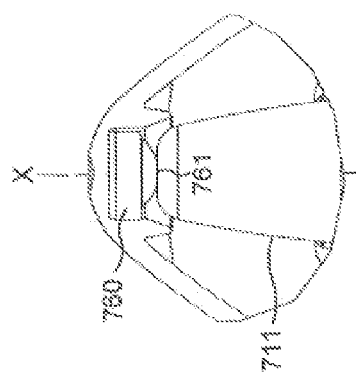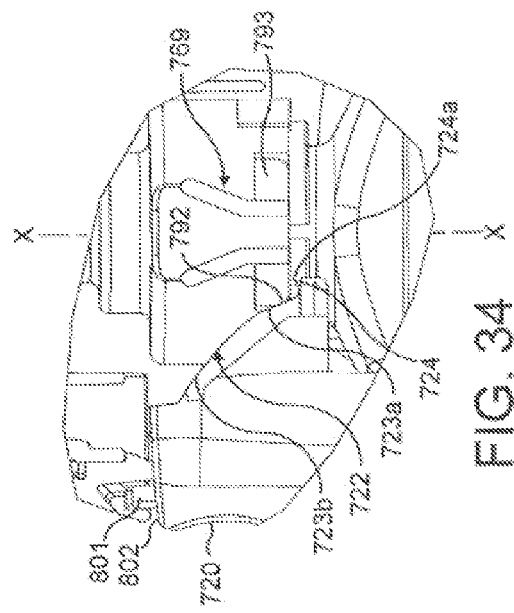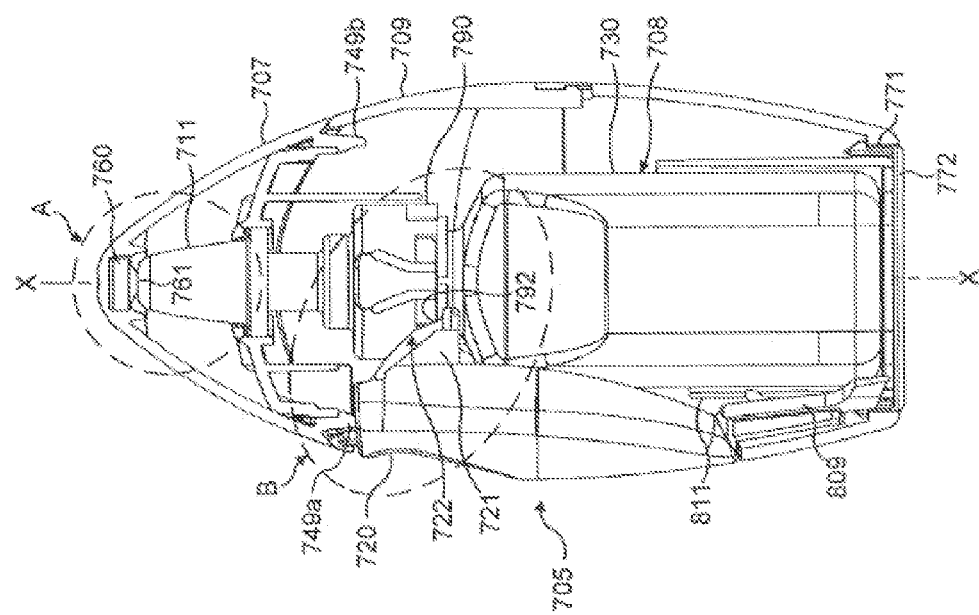

FLUID DISPENSING DEVICE

CROSS-REFERENCE TO RELATED APPLICATIONS

The present application is a Continuation of U.S. patent application Ser. No. 10/577,977, filed on May 3, 2006, which issued as U.S. Pat. No. 8,752,543 on Jun. 17, 2014; which was a US National Phase application filed pursuant to 35 U.S.C. §371 of International Patent Application No. PCT/GB2004/004626 filed Nov. 2, 2004; which claims priority from Application No. 0325629.4 filed on Nov. 3, 2003; Application No. 0405477.1 filed on 11 Mar. 2004; and Application No. 0420539.9 filed on Sep. 17, 2004, each filed in the United Kingdom; and each of which are incorporated herein by reference.

BACKGROUND OF THE INVENTION

The present invention relates to a medicament dispenser and in particular to a fluid dispensing device for use as a nasal inhaler.

It is known to provide a medicament dispenser, in which fluid spray is dispensed via a nozzle or orifice upon the application of a force by a user to an actuation lever or button. Such devices may be arranged to dispense a single dose or may alternatively be arranged with a reservoir containing several doses to be dispensed.

It is a problem with such a prior art sprays that if the actuator is moved in a slow or unpredictable manner a strong and well-defined spray may not be produced and so the medicament formulation may not be effectively dispensed. This problem is particularly significant where an actuator (e.g. a lever) acts on a pump mechanism such as to pump the fluid to be sprayed from a container. In this case, slow or unpredictable actuation results in a slow or unpredictable actuation of the pump and hence, unreliable spray characteristics.

The Applicant has now appreciated that the problem of producing a well-defined spray may be significant where the medicament formulation is in the form of a relatively viscous formulation. The formulation may be formulated as a solution formulation, or as a suspension formulation that comprises particles of medicament suspended in a suspending formulation (which acts as a 'carrier' to suspend the medicament particles). A suspending formulation generally has a relatively high viscosity, as can assist with suspension of the medicament particles, and may comprise agents to enhance/control the viscosity thereof.

By way of solving or alleviating the above-described problems, the dispensing device herein includes a 'commitment' feature, which prevents actuation of the pump in the absence of the application of pre-determined force to a finger operable actuator.

It is an aim of this invention to provide a fluid dispensing device that is easier to use and in particular a device which provides a more efficient dispensing of fluid medicament formulation, particularly one which is viscous in nature.

SUMMARY OF THE INVENTION

According to a first aspect of the invention there is provided a fluid dispensing device for spraying a fluid into a body cavity comprising a housing, a nozzle for insertion into a body cavity, a fluid discharge device moveably housed within the housing, the fluid discharge device having a longitudinal axis and comprising a container containing a fluid medicament formulation to be dispensed and a compression pump having a suction inlet located within the container and a discharge tube extending along the longitudinal axis for transferring fluid from the pump to the nozzle and finger operable means moveable with respect to the longitudinal axis of the fluid discharge device to apply a force to the container to move the container along the longitudinal axis towards the nozzle so as to actuate the compression pump wherein a pre-load means is provided to prevent actuation of the compression pump until a pre-determined force is applied to the finger operable means, and wherein said fluid medicament formulation has a viscosity of from 10 to 2000 mPa·s at 25° C.

In one aspect, the fluid medicament formulation is formulated as a solution formulation. In another aspect, the fluid medicament formulation is formulated as a suspension formulation comprising a suspension of active medicament particles in an inert suspending formulation.

It will be appreciated that in general operation of the fluid dispensing device relative movement between the container (e.g. a hollow casing defining a fluid reservoir) and the compression pump acts such as to pump fluid from the container into the nozzle for dispensing therefrom.

In aspects, the pumping is metered. For example, each pumping action results in delivery of a single dose of fluid from the container to the nozzle.

Suitably for metered delivery, the compression pump includes a plunger, which is slidable in a metering chamber located within the hollow casing, the metering chamber being sized to accommodate a single dose of fluid. The container typically contains several doses of fluid.

The term finger operable means is meant to encompass such means operable by action of the finger or thumb, or combinations thereof of a typical user (e.g. an adult or child patient).

In one aspect, the finger operable means is moveable transversely with respect to the longitudinal axis of the fluid discharge device to apply a force directly or indirectly to the container. In another aspect, the finger operable means is moveable generally parallel to the longitudinal axis of the fluid discharge device to apply a force directly or indirectly to the container. Other movements intermediate between 'transverse' and 'parallel' are envisaged. In variations, the finger operable means may contact the container or be coupled thereto to enable the necessary transfer of force.

Suitably, the finger operable means is arranged to apply mechanical advantage. That is to say, the finger operable means applies mechanical advantage to the user force to adjust (generally, to enhance or smooth) the force experienced by the container. The mechanical advantage may in one aspect, be provided in either a uniform manner such as by a constant mechanical advantage enhancement, for example by a ratio of from 1.5:1 to 10:1 (enhanced force:initial force), more typically from 2:1 to 5:1. In another aspect, the mechanical advantage is applied in a non-constant manner such as progressive increase or progressive decrease of mechanical advantage over the applied force cycle. The exact profile of mechanical advantage variation may be readily determined by reference to the desired spray profile and all relevant characteristics of the device and formulation to be sprayed (e.g. viscosity and density).

Suitably, the finger operable means has a form, which naturally gives rise to mechanical advantage such as a lever, cam or screw form.

The finger operable means may comprise of at least one lever pivotally connected to part of the housing and arranged to transfer force to the container (e.g. acting directly thereupon) so as to urge the container towards the nozzle when the or each lever is moved by a user.

In one aspect, there are two opposing levers, each of which pivotally connect to part of the housing and may be arranged to act upon the container so as to urge the container towards the nozzle when the two levers are squeezed together by a user.

Alternatively, the finger operable means may comprise of at least one lever to apply a force to an actuating means used to move the container towards the nozzle so as to actuate the pump.

In which case the or each lever may be pivotally supported at a lower end within the housing and the actuating means may in aspects be connected to a neck of the container (e.g. formed as a collar thereto).

Suitably, there may be two opposing levers, each of which is pivotally supported near a lower end of the housing and may be arranged to act upon the actuating means so as to urge the container towards the nozzle when the two levers are squeezed together by a user.

Alternatively, the finger operable means may comprise of at least one lever slidably supported within the housing to apply a force to the container so as to move the container towards the nozzle and actuate the compression pump.

The pre-load means acts such as to prevent actuation of the compression pump until a pre-determined force is applied to the finger operable means. The pre-determined force may thus, be thought of as a 'threshold' or 'barrier' force which must first be overcome before actuation of the compression pump can occur.

The quantum of pre-determined force that is to be overcome before actuation of the compression pump is enabled is selected according to various factors including characteristics of the pump, typical user profile, nature of the fluid and the desired spray characteristics.

Typically, the pre-determined force is in the range from 5 to 45N, more typically from 10 to 25N. That is to say, typically from 5 to 30N, more typically from 10 to 25N of force must be applied to the finger operable means before actuation of the compression pump is enabled. Such values tend to correspond to a force which prevents a suitable 'barrier force' to a weak, nondescript or unintended finger movement whilst readily being overcome by the determined finger (or thumb) action of a user. It will be appreciated that if the device is designed for use by a child or elderly patient it may have a lower pre-determined force than that designed for adult usage.

In accordance with a first embodiment of the invention the pre-load means is physically interposed between the or each finger operable means (e.g. lever) and the container.

In which case, the pre-load means may comprise of a step formed on the container which must be ridden over by the or each lever before the compression pump can be actuated wherein the step is over-ridden when the pre-determined force is applied to the or each lever.

Alternatively, the pre-load means may comprise of a step formed on the or each finger operable means (e.g. lever) which must be ridden over by the container before the compression pump can be actuated wherein the step is over-ridden when the pre-determined force is applied to the or each lever.

In yet a further alternative, the pre-load means may comprise of at least one detent formed on one of the container or the or each finger operable means (e.g. a lever) and a recess formed on the other of the container or the or each lever wherein the or each detent is able to ride out of the recess with which it is engaged when the pre-determined force is applied to the or each lever.

According to a second embodiment of the invention the pre-load means is interposed between the housing and the container.

In which case, the pre-load means may comprise of one or more detents formed on the container for engagement with part of the housing, the or all of the detents being disengageable from the housing when the pre-determined force is applied to the finger operable means so as to allow the compression pump to be actuated.

Alternatively, the pre-load means may comprise of one or more detents formed on the housing for engagement with part of the container, the or all of the detents being disengageable from the container when the pre-determined force is applied to the finger operable means so as to allow the compression pump to be actuated.

According to a third embodiment of the invention the pre-load means is interposed between the container and the discharge tube.

In which case, the pre-load means may comprises of a step formed on the discharge tube and at least one latching member attached to the container, the arrangement being such that, when the pre-determined force is applied to the finger operable means, the or each latching member is able to ride over the step so as to allow the compression pump to be actuated.

Alternatively, the pre-load means may comprise of a recess formed on the discharge tube and at least one latching member attached to the container, the arrangement being such that, when the pre-determined force is applied to the finger operable means, the or each latching member is able to ride out of the recess so as to allow the compression pump to be actuated.

According to a fourth embodiment of the invention the pre-load means is interposed between the housing and the or each finger operable means (e.g. lever).

In which case, the pre-load means may comprise of at least one detent formed on the housing for engagement with each lever, the or all of the detents being disengageable from the respective lever when the pre-determined force is applied to the or each lever so as to allow the compression pump to be actuated.

Alternatively, the pre-load means may comprise of at least one detent formed on each lever for engagement with part of the housing, the or all of the detents being disengageable from the housing when the pre-determined force is applied to the or each lever so as to allow the compression pump to be actuated.

According to a fifth embodiment of the invention the pre-load means is interposed between the actuating means and the housing.

In which case, the pre-load means may comprise of at least one detent formed on part of the actuating means for engagement with part of the housing, the or all of the detents being disengageable from the housing when the pre-determined force is applied to the or each finger operable means (e.g. lever) so as to allow the compression pump to be actuated.

Alternatively, the pre-load means may comprise of at least one detent formed on part of the housing each detent being arranged for engagement with a complementary recess formed on part of the actuating means, each detent being disengageable from its respective recess when the pre-determined force is applied to the or each finger operable means (e.g. lever) so as to allow the compression pump to be actuated.

According to a sixth embodiment of the invention the pre-load means is interposed between the or each finger operable means (e.g. lever) and the respective actuating means.

In which case, the pre-load means may comprise of at least one detent formed on the or each lever for engagement with a respective recess formed on part of the actuating means, each detent being disengageable from its respective complementary recess when the pre-determined force is applied to the lever so as to allow the compression pump to be actuated.

Alternatively, the pre-load means comprises of at least one detent formed on each actuating means for engagement with a recess formed on a respective lever, each detent being disengageable from its respective complementary recess when the pre-determined force is applied to the lever so as to allow the compression pump to be actuated.

As yet a further alternative, the pre-load means (e.g. comprised at the finger operable means) defines a variable mechanical ratio such that until the pre-determined force is applied to the or each finger operable means (e.g. a lever) no significant force is transferred to the container along the longitudinal axis. The variable mechanical ratio is suitably defined by the profile of interaction of a surface of the finger operable means with a follower element provided to the container or a fitting provided thereto (e.g. a collar).

In one aspect, the variable mechanical ratio defines a 'two step' profile characterized by an initial 'high force' (e.g. high gradient) profile (defining the pre-load force, to be overcome) and a subsequent 'low force' (e.g. low gradient) profile.

In one particular aspect, the 'high force' and 'low force' profiles are linear (i.e. straight lines) and have a sharp break point therebetween.

In another particular aspect, the 'high force' and 'low force' profiles are curved and have a smooth/gradual break point therebetween.

In a preferred aspect, the 'high force' and 'low force' profiles have part-circle profile forms (e.g. as would be defined be overlapping circles of different radii and different centres) and have a smooth/gradual break point therebetween.

The fluid dispensing device may alternatively comprise of a finger operable means in the form of a single lever and the pre-load means may further comprise of a spring interposed between the lever and the container, the spring being used to urge the container towards the nozzle so as to actuate the compression pump.

In which case the spring may be compressed by movement of the lever until the pre-determined force is applied (i.e. by a combination of user-applied force and stored spring force), at which point the threshold of the pre-load means used to prevent actuation of the compression pump is overcome by the force being applied to the container such that the container moves rapidly towards the nozzle so as to actuate the compression pump.

Suitably, the fluid dispensing device is additionally provided with force modifying means for modifying the force applied to the container. That is to say, means for modifying the force applied to (and therefore, ultimately acting on) the container compared to that force directly applied to the finger operable means by the user.

Suitably, the force modifying means acts such as to amplify the force applied (i.e. it comprises force amplifying means). The amplification may be provided in either a uniform manner such as by a constant amplification, for example by a ratio of from 1.5:1 to 10:1 (amplified force:initial force; i.e. degree of amplification of from 1.5 to 10), more typically from 2:1 to 5:1. In another aspect, the amplification is applied in a non-constant manner such as progressive increase or progressive decrease of mechanical advantage over the applied force cycle.

The exact profile of force modification may be readily determined by reference to the desired spray profile and all relevant characteristics of the device and formulation to be sprayed (e.g. viscosity and density).

The force modifying means may in one aspect, be integral with the finger operable means. In this aspect, the force modifying means may comprise an aspect of the finger operable means shaped to give rise to a mechanical advantage (e.g. a lever, cam or screw feature).

In another aspect, the force modifying means is located non-integral with the finger operable means, and typically between the finger operable means and the container. Again this aspect, the force modifying means may comprise an aspect of the finger operable means shaped to give rise to a mechanical advantage (e.g. a lever, cam or screw feature).

In one aspect, the force modifying means only acts (i.e. only acts to modify the user applied force) once the pre-determined force has been overcome. In preferred aspects, the modifying force acts such that once the pre-determined force has been overcome the force applied to the container is either relatively constant or increases on a relatively constant basis.

In one particular aspect, the force modifying means additionally comprises a stop feature, which acts to stop force being applied to the container once either a particular maximum force is reached or more typically, once the container has been moved a particular distance. In one aspect, the stop functions to prevent excess force being applied to the compression pump.

The fluid dispensing device herein is particularly suitable for dispensing a fluid medicament formulation. The container therefore contains a fluid medicament formulation e.g. formulated either as a solution formulation or as a suspension formulation comprising a suspension of active medicament particles in an inert suspending formulation.

The medicament particles comprise an active medicament, which may be selected from, for example, analgesics, e.g. codeine, dihydromorphine, ergotamine, fentanyl or morphine; anginal preparations, e.g., diltiazem; antiallergics, e.g., cromoglycate (eg as the sodium salt), ketotifen or nedocromil (eg as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone (eg as the furoate ester), ciclesonide, triamcinolone (eg as the acetonide), 6α,9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α,9α-Difluoro-17α-[(2-furanylcarbonyl)oxy]-11β-hydroxy-16α-methyl-3-oxo-androsta-1,4-diene-17β-carbothioic acid S-fluoromethyl ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl] amino]ethyl-2(3H)-benzothiazolone; PDE4 inhibitors eg cilomilast or roflumilast; leukotriene antagonists eg montelukast, pranlukast and zafirlukast; [adenosine 2a agonists, eg 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g. as maleate)]*; [α4 integrin inhibitors eg (2S)-3-[4-({[4-(aminocarbonyl)-1-piperidinyl] carbonyl}oxy)phenyl]-2-[((2S)-4-methyl-2-{[2-(2-methylphenoxy) acetyl]amino}pentanoyl)amino]propanoic acid (e.g as free acid or potassium salt)]*, diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagons. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant.

Preferably, the active medicament is an anti-inflammatory compound for the treatment of inflammatory disorders or diseases such as asthma and rhinitis.

In one aspect, the medicament is a glucocorticoid compound, which has anti-inflammatory properties. One suitable glucocorticoid compound has the chemical name: 6α,9α-Difluoro-17α-(1-oxopropoxy)-11β-hydroxy-16α-methyl-3-oxo-androsta-1,4-diene-17β-carbothioic acid S-fluoromethyl ester (fluticasone propionate). Another suitable glucocorticoid compound has the chemical name: 6α,9α-difluoro-17α-[(2-furanylcarbonyl)oxy]-11β-hydroxy-16α-methyl-3-oxo-androsta-1,4-diene-17β-carbothioic acid S-fluoromethyl ester. A further suitable glucocorticoid compound has the chemical name: 6α,9α-Difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester.

Other suitable anti-inflammatory compounds include NSAIDs e.g. PDE4 inhibitors, leukotriene antagonists, iNOS inhibitors, tryptase and elastase inhibitors, beta-2 integrin antagonists and adenosine 2a agonists.

The medicament is in particulate form. The particulate medicament suitably has a mass mean diameter (MMD) of less than 20 μm, preferably between 0.5-10 μm, especially between 1-5 μm. If particle size reduction is necessary, this may be achieved by techniques such as micronisation, wet bead milling and/or microfluidisation.

Suitable medicament particles may be produced by conventional techniques, for example by micronisation, milling or sieving. Additionally, medicament and/or excipient powders may be engineered with particular densities, size ranges, or characteristics. Particles may comprise active agents, surfactants, wall forming materials, or other components considered desirable by those of ordinary skill.

In one aspect, the fluid medicament formulation is formulated as a medicament suspension formulation comprising a suspension of active medicament particles in an inert suspending formulation, optionally containing other pharmaceutically acceptable additive components.

The inert suspending formulation is typically aqueous and comprises one or more excipients. By the term "excipient", herein, is meant substantially inert materials that are non-toxic and do not interact with other components of a composition in a deleterious manner including, but not limited to, pharmaceutical grades of carbohydrates, organic and inorganic salts, polymers, amino acids, phospholipids, wetting agents, emulsifiers, surfactants, poloxamers, pluronics, and ion exchange resins, thixotropic agents and combinations thereof.

Suitable carbohydrates include monosaccharides including fructose; disaccharides, such as, but not limited to lactose, and combinations and derivatives thereof; polysaccharides, such as, but not limited to, cellulose and combinations and derivatives thereof; oligosaccharides, such as, but not limited to, dextrins, and combinations and derivatives thereof; polyols, such as but not limited to sorbitol, and combinations and derivatives thereof.

Suitable organic and inorganic salts include sodium or calcium phosphates, magnesium stearate, and combinations and derivatives thereof.

Suitable polymers include natural biodegradable protein polymers, including, but not limited to, gelatin and combinations and derivatives thereof; natural biodegradable polysaccharide polymers, including, but not limited to, chitin and starch, crosslinked starch and combinations and derivatives thereof; semisynthetic biodegradable polymers, including, but not limited to, derivatives of chitosan; and synthetic biodegradable polymers, including, but not limited to, polyethylene glycols (PEG), polylactic acid (PLA), synthetic polymers including but not limited to polyvinyl alcohol and combinations and derivatives thereof;

Suitable amino acids include non-polar amino acids, such as leucine and combinations and derivatives thereof. Suitable phospholipids include lecithins and combinations and derivatives thereof.

Suitable wetting agents, surfactants and/or emulsifiers include gum acacia, cholesterol, fatty acids including combinations and derivatives thereof. Suitable poloxamers and/or Pluronics include poloxamer 188, Pluronic® F-108, and combinations and derivations thereof. Suitable ion exchange resins include amberlite IR120 and combinations and derivatives thereof;

Preferred suspension formulations herein comprise an aqueous suspension of particulate medicament and one or more additional components selected from the group consisting of suspending agents, preservatives, wetting agents, viscosity enhancing agents and isotonicity adjusting agents.

Suitable suspending agents include carboxymethylcellulose, veegum, tragacanth, bentonite, methylcellulose and polyethylene glycols.

Particular suspending agents are those sold under the trade name Miglyol by Condea Chemie GmbH which comprise ester oils of saturated coconut and palm oil-derived caprylic and capric fatty acids and glycerin or propylene glycol. Particular examples include Miglyol 810, Miglyol 812 (caprylic/capric triglyceride); Miglyol 818 (caprylic/capric/linoleic triglyceride); Miglyol 829 (caprylic/capric/succinic triglyceride); and Miglyol 840 (propylene glycol dicaprylate/dicaprate).

Suitable preservatives include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts and polymyxin.

Suitable wetting agents function to wet the particles of medicament to facilitate dispersion thereof in the aqueous phase of the composition. Examples of wetting agents that can be used are fatty alcohols, esters and ethers. Preferably, the wetting agent is a hydrophilic, non-ionic surfactant, most preferably polyoxyethylene (20) sorbitan monooleate (supplied as the branded product Polysorbate 80).

Suitable viscosity enhancing agents include carboxymethylcellulose, veegum, tragacanth, bentonite, hydroxypropylmethylcellulose, hydroxypropylcellulose, hydroxyethylcellulose, poloxamers (eg. poloxamer 407), polyethylene glycols, alginates xanthym gums, carageenans and carbopols.

Suitable isotonicity adjusting agents act such as to achieve isotonicity with body fluids (e.g. fluids of the nasal cavity), resulting in reduced levels of irritancy associated with many nasal formulations. Examples of suitable isotonicity adjusting agents are sodium chloride, dextrose and calcium chloride.

Suitable thixotropic agents include that sold under the trade name Avicel RC951 NF, which comprises a mixture of carboxymethylcellulose sodium salt (8.3% to 13.8%) and microcrystalline cellulose. Thixotropic agents tend to make the formulation more viscous when static, but to become less viscous when kinetic energy is applied (e.g. on shaking the container).

In another aspect, the fluid medicament formulation is formulated as a solution medicament formulation. The formulation may be an aqueous, or in particular embodiments, a non-aqueous formulation. Suitable solution formulations may comprise a solubilising agent such as a surfactant.

Suitable surfactants include α-[4-(1,1,3,3-tetramethylbutyl)phenyl]-ω-hydroxypoly(oxy-1,2-ethanediyl) polymers including those of the Triton series e.g. Triton X-100, Triton X-114 and Triton X-305 in which the X number is broadly indicative of the average number of ethoxy repeating units in the polymer (typically around 7-70, particularly around 7-30 especially around 7-10) and 4-(1,1,3,3-tetramethylbutyl)phenol polymers with formaldehyde and oxirane such as those having a relative molecular weight of 3500-5000 especially 4000-4700, particularly Tyloxapol. The surfactant is typically employed in a concentration of around 0.5-10%, preferably around 2-5% w/w based on weight of formulation.

Suitable solution formulations may also comprise hydroxyl containing organic co-solvating agents include glycols such as polyethylene glycols (eg PEG 200) and propylene glycol; sugars such as dextrose; and ethanol. Dextrose and polyethylene glycol (eg PEG 200) are preferred, particularly dextrose. Propylene glycol is preferably used in an amount of no more than 20%, especially no more than 10% and is most preferably avoided altogether. Ethanol is preferably avoided. The hydroxyl containing organic co-solvating agents are typically employed at a concentration of 0.1-20% e.g. 0.5-10%, e.g. around 1-5% w/w based on weight of formulation.

Suitable solution formulations may also comprise solubilising agents such as polysorbate, glycerine, benzyl alcohol, polyoxyethylene castor oils derivatives, polyethylene glycol and polyoxyethylene alkyl ethers (e.g. Cremophors, Brij). Other solubilising agents are those sold under the trade name Miglyol by Condea Chemie GmbH which comprise ester oils of saturated coconut and palm oil-derived caprylic and capric fatty acids and glycerin or propylene glycol.

One non-aqueous solution formulation is based upon Miglyol (trade name) either used neat to solubilise the medicament substance, or as a mixture with propylene glycol and/or polyethylene glycol.

Suitable suspension or solution formulations may be stabilised (e.g. using hydrochloric acid or sodium hydroxide) by appropriate selection of pH. Typically, the pH will be adjusted to between 4.5 and 7.5, preferably between 5.0 and 7.0, especially around 6 to 6.5.

The fluid medicament formulation herein has a viscosity of from 10 to 2000 mPa·s (10 to 2000 centipoise), particularly from 20 to 1000 mPa·s (20 to 1000 centipoise), such as from 50 to 1000 mPa·s (50 to 1000 centipoise) at 25° C.

The viscosity of the inert suspending formulation herein is measured by any suitable method.

One suitable method for measuring viscosity is by use of a Brookfield (trade name) viscometer using an appropriate choice of paddle/spindle and volume of liquid as guided by user manual instructions.

Another suitable method for measuring viscosity is by use of a suitable rheometer such as TA Instruments Advanced Rheometer AR500, Techne Tempette Junior TE-8J Water Bath System. In this method, the sample of fluid medicament formulation is pre-sheared at 20 Pa immediately prior to analysis. The shear rate (1/s) is measured over the following linear shear stress range: 0.2 to 20 Pa over a period of 1 minute. The profile thus obtained is modeled using the Herschel-Bulkley model. Using this modeled data, the viscosity at a shear rate of 250 1/s is calculated.

The method suitably employs a parallel plate, using e.g. Standard Acrylic Parallel Plate (60 mm) (Acrylic 5660, 6 cm Flat Plate). Suitable test method conditions are:
Temperature: 25° C.
Sample size: 1.5 ml
Gap: 250 micrometers
   Suitable flow procedure settings are:
   (A) Conditioning Step:
   (i) Initial temperature=25° C.
   (ii) Pre-shear Shear Stress=20 Pa
      Pre-shear duration=1 minute
   (iii) Duration of equilibration=10 seconds
   (B) Continuous Ramp Step 1:
   (i) Test type=Continuous ramp
   (ii) Test settings:
      Ramp=Shear stress (Pa) from 0.2358 Pa to 20 Pa
      Duration=1 minute
      Mode=Linear
   (iii) Sampling points=12
   (iv) Temperature=25° C.

Where the fluid medicament formulation comprises a thixotropic component, or otherwise has a viscosity that is significantly influenced by kinetic energy supplied to it, the appropriate measured viscosity value is the minimum constant value measured. In this case, a high shear test method is particularly suitable, so that the measured viscosity values will be close to their minimum possible values.

Embodiments are envisaged in which the fluid discharge device is reversibly removable from the housing of the fluid dispensing device. In such embodiments the fluid discharge device comprises a housing assembly and fluid discharge device receivable thereby.

Suitably, a dispensing orifice of the nozzle is provided with a reversible stopper. The stopper acts such as to prevent drain back of delivered fluid from the nozzle (in particular, from the area at the tip of the nozzle and generally adjacent to the dispensing orifice).

Suitably, the stopper is reversibly mountable to the nozzle (e.g. at the tip) to enable reversible sealing of the dispensing orifice thereof. In use, such sealing acts such as to minimise drain back of fluid from the dispensing orifice through the interior of the nozzle.

The stopper may have any suitable shape including disc shaped, wherein the disc may be flat, or in aspects have a convex or concave form.

It will be appreciated that the stopper is generally shaped for effective sealing engagement with the tip of the dispensing nozzle (i.e. that area proximal to the dispensing orifice) and therefore that the shaping of the stopper may be arranged to inversely mirror that of the nozzle tip.

The stopper may be formed from any suitable material including those with plastic properties, particularly those with resilient properties. Stoppers made from synthetic and naturally occurring polymers including rubber are herein envisaged.

Suitable stopper insert forms may be formed in a variety of ways. In one aspect, a rubber disc-shaped stopper is stamped from a sheet of rubber. In another aspect, a disc-shaped stopper is moulded (e.g. by an injection moulding process).

Suitably, the fluid dispensing device may further comprise a protective end cap having an inner surface for engagement with the housing. The end cap is moveable from a first position in which it covers the nozzle to a second position in which the nozzle is uncovered.

Suitably, the stopper locates on the end cap such that when the end cap is in the first (i.e. protective) position the stopper engages the nozzle to seal the nozzle orifice. In the second (i.e. in-use position) the stopper is disengaged from the nozzle such that the nozzle orifice is no longer sealed.

The stopper may form an integral part of the end cap or alternatively, the stopper may mount to the end cap. Any suitable method of mounting is envisaged including adhesive, snap-fit and weld mounting.

In general, the stopper locates in the inner part of the end cap. In one aspect, the inner part of the end cap is provided with annular walls defining a cavity for receipt of the stopper as an insert thereto. The stopper insert may be simply be mechanically inserted or it may be adhesively or otherwise fixed.

Suitable stopper insert forms may be formed in a variety of ways. In one aspect, a rubber disc-shaped stopper is stamped from a sheet of rubber. In another aspect, a disc-shaped stopper is moulded (e.g. by an injection moulding process). In a further aspect, the protective end cap is moulded and the stopper is then moulded within the formed end cap (i.e. a 'two shot' moulding process).

There is also provided a housing assembly for reversible receipt of a fluid discharge device for spraying a fluid into a body cavity, said fluid discharge device having a longitudinal axis and comprising a container containing a fluid medicament formulation to be dispensed and a compression pump having a suction inlet located within the container and a discharge tube extending along the longitudinal axis for transferring fluid from the pump to the nozzle, the housing assembly comprising a housing, a nozzle for insertion into a body cavity and finger operable means moveable transversely with respect to the longitudinal axis of the fluid discharge device to apply a force to the container to move the container along the longitudinal axis towards the nozzle so as to actuate the compression pump wherein a pre-load means is provided to prevent actuation of the compression pump until a pre-determined force is applied to the finger operable means, and wherein said fluid medicament formulation has a viscosity of from 10 to 2000 mPa·s at 25° C.

According to another aspect of the present invention there is provided a kit of parts comprising a housing assembly as described above and a fluid discharge device receivable thereby. The fluid discharge device has a longitudinal axis and comprises a container for storing the fluid to be dispensed and a compression pump having a suction inlet located within the container and a discharge tube extending along the longitudinal axis for transferring fluid from the pump to the nozzle.

Suitably, the fluid discharge device herein comprises a pump such as a pre-compression pump. Suitable pumps include VP3, VP7 or modifications, model manufactured by Valois SA. Typically, such pre-compression pumps are typically used with a bottle (glass or plastic) container capable of holding 8-50 ml of a formulation. Each spray will typically deliver 25-150 µl, particularly 50-100 µl of such a formulation and the device is therefore typically capable of providing at least 50 (e.g. 60 or 100) metered doses.

Other suitable fluid discharge devices include those sold by Erich Pfeiffer GmbH, Rexam-Sofab and Saint-Cobain Calmar GmbH.

It is also envisaged that the housing assembly could be supplied as a separate item, into which a user or pharmacist later fits a suitable fluid discharge device.

According to a further aspect of the present invention there is provided a fluid dispensing device for dispensing a fluid medicament formulation having:— a dispensing outlet from which the fluid medicament formulation is dispensable, a container containing a fluid medicament formulation to be dispensed;

a dispensing member mounted for movement in a dispensing direction along an axis from a first position to a second position which causes a dose of the fluid medicament formulation in the container to be dispensed from the dispensing outlet, and a finger-operable actuator member mounted for movement in an actuating direction which is generally transverse to the axis, wherein the actuator member has at least one cam surface and the dispensing member has at least one cam follower surface, wherein the actuator member is movable in the actuating direction to cause the at least one cam surface to bear against the at least one cam follower surface to force the at least one cam follower surface to ride over the cam surface to cam the dispensing member in the dispensing direction from the first position to the second position, wherein the at least one cam surface has a commitment section, oriented at a first angle to the axis, and an adjacent drive section, which is oriented at a second angle to the axis which is greater than the first angle, wherein the device is configured and arranged such that, in use, the at least one cam follower surface successively rides over the commitment and drive sections of the at least one cam surface, on movement of the actuator member in the actuating direction, to cam the dispensing member from the first position to the second position, and wherein the first angle is selected such that a minimum actuating force is required to be applied to the actuator member to cause the at least one cam follower surface to ride over the commitment section onto the drive section, and wherein said fluid medicament formulation has a viscosity of from 10 to 2000 mPa·s at 25° C.

Suitably, the first angle is in the range of about 20-35°.

Suitably, the commitment section is planar.

Suitably, the minimum actuating force is in the range of about 5-45N, particularly 20-45N.

Suitably, the second angle is in the range of about 40-60°.

Suitably, the drive section has an arcuate transition portion contiguous with the commitment section.

Suitably, the transition portion has a radius of curvature in the range of about 1-5 mm.

Suitably, the drive section is arcuate.

Suitably, the drive section has a first portion of a first radius of curvature contiguous with the commitment section and a second portion, contiguous with the first portion, of a second radius of curvature which is greater than the first radius of curvature.

Suitably, the drive section consists of the first and second portions.

Suitably, the commitment section is of a first length and the drive section is of a second length greater than the first length.

Suitably, the minimum actuating force is in the range of about 25-40N.

Suitably, at least one cam follower surface is arcuate.

Suitably, the second portion has a radius of curvature in the range of about 15-40 mm Suitably, the actuator member is mounted in the device for movement on an arcuate path in the actuating direction.

Suitably, the device is configured and arranged such that the first angle to the axis becomes steeper as the actuator member moves in the actuating direction.

Suitably, the device is configured and arranged such that the second angle to the axis remains constant, or substantially constant, as the actuator member moves in the actuating direction.

Suitably, the actuator member is mounted for pivotal movement about a first end thereof and the at least one cam surface is disposed on the actuator member remote from the first end.

Suitably, the dispensing member is a dispensing container in which the supply of the fluid product is contained.

Suitably, the dispensing direction is an upward direction and the first end of the actuator member is a lower end thereof.

Suitably, the at least one cam follower surface is disposed towards an upper end of the dispensing member.

Suitably, the dispensing container has a pump, which is caused to pump the dose of the fluid product from the dispensing outlet in response to the dispensing container being moved in the dispensing direction by the actuator member.

Suitably, the actuator member is the sole actuator member.

Suitably, the dispensing outlet is in a nozzle sized and shaped for insertion into a body cavity.

Suitably, the nozzle is for insertion into a nostril of a human or animal body.

Suitably, the dispensing member and housing have co-operating guide members for guiding movement of the dispensing member along the axis.

Suitably, the co-operating guide members prevent rotation of the dispensing member about the axis.

Suitably, one of the guide members comprises a runner and the other guide member comprises a track for the runner.

BRIEF DESCRIPTION OF THE SEVERAL VIEWS OF THE DRAWINGS

The invention will now be described further with reference to the accompanying Figures of drawings in which:

FIG. 14 is a front view of a fluid dispensing device having an alternative mechanism to actuate the fluid discharge device to that shown in FIG. 1 and having a pre-load means according to the fourth embodiment of the invention with an end cap removed;

FIG. 15 is a front view of the fluid dispensing device shown in FIG. 14 with an end cap in place;

FIG. 19b is an enlarged perspective view of the collar of FIG. 19a;

FIG. 20 is a front view of the fluid dispensing device shown in FIGS. 18 and 19 but showing the use of a pre-load means according to the fourth embodiment of the invention;

FIG. 21 is a side view in the direction of the arrow 'P' on FIG. 20;

FIG. 32 is a partial longitudinal sectional view of the fluid dispensing device of FIG. 30;

FIG. 33 is an enlarged view of area A in FIG. 32;

FIG. 34 is an enlarged view of area B in FIG. 32;

FIG. 41 b is further view of an embodiment of a lever of the present invention having a dual gradient profile.

DETAILED DESCRIPTION

Figure 1:
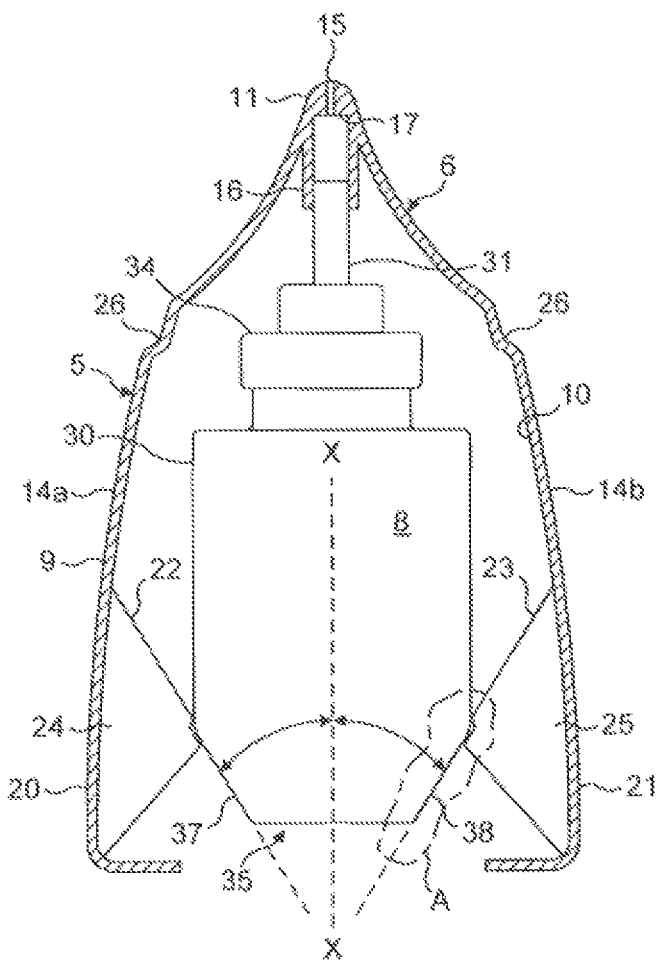
FIG. 1 is a cross-section through a fluid dispensing device including a fluid discharge device having a pre-load means according to a first embodiment of the invention in a ready for use state.
Figure 2A:
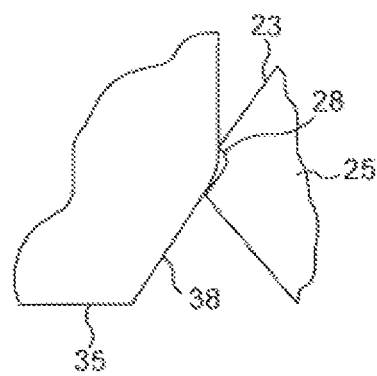
FIG. 2a is an enlarged view of the area indicated by the arrow 'A' on FIG. 1.
Figure 3:
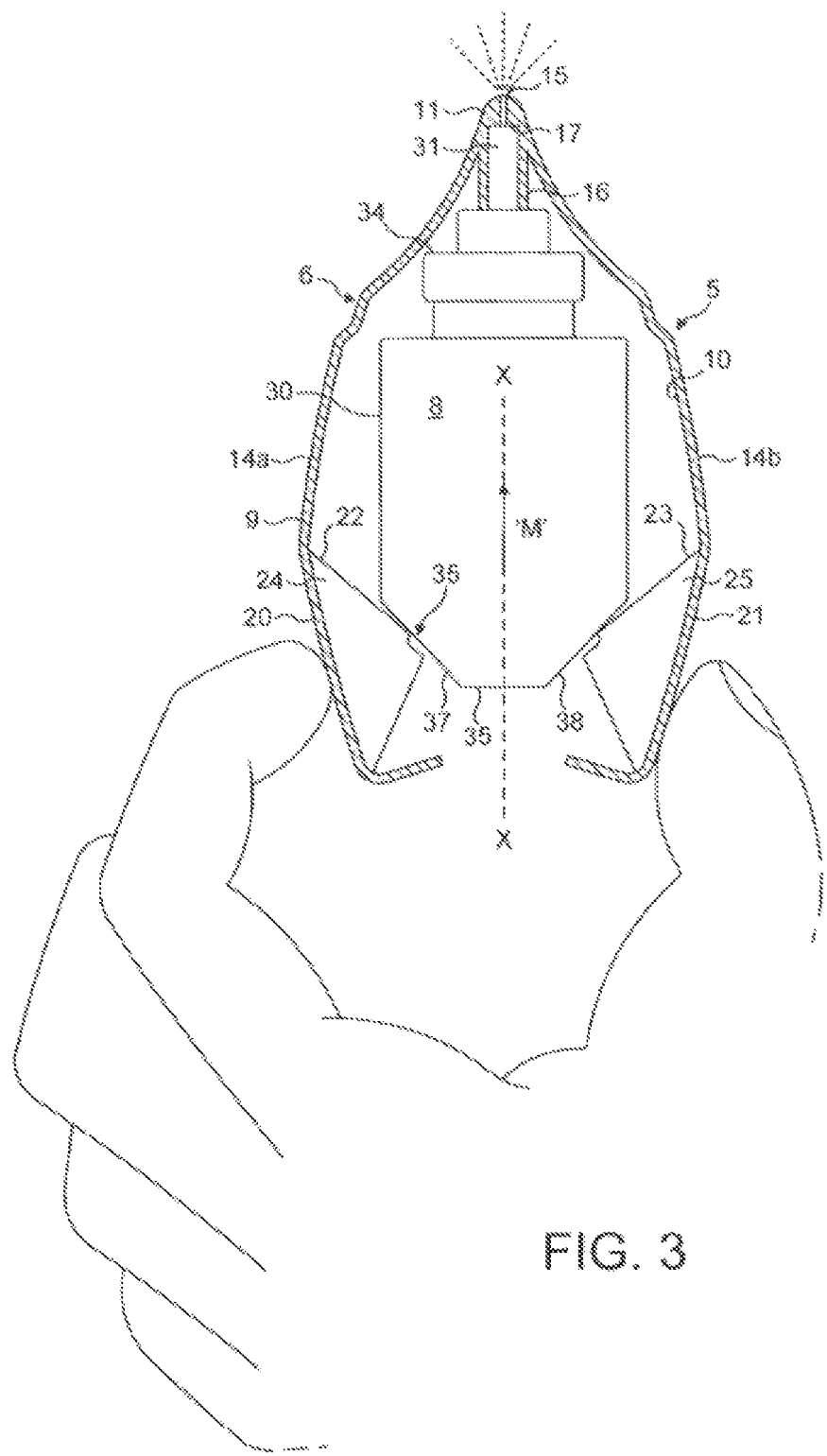
FIG. 3 is a cross-section similar to that of FIG. 1 but showing the fluid dispensing device in use.

With reference to FIGS. 1, 2a and 3 there is shown a fluid dispensing device 5 for spraying a fluid into a body cavity comprising a housing 9, a nozzle 11 for insertion into a body cavity, a fluid discharge device 8 moveably housed within the housing 9, the fluid discharge device 9 having a longitudinal axis and comprising a container 30 for storing the fluid to be dispensed and a compression pump having a suction inlet located within the container 30 and a discharge tube 31 extending along the longitudinal axis for transferring fluid from the compression pump to the nozzle 11 and finger operable means moveable transversely with respect to the longitudinal axis of the fluid discharge device to apply a force to the container 30 to move the container 30 along the longitudinal axis towards the nozzle 11 so as to actuate the compression pump and a pre-load means to prevent actuation of the compression pump until a pre-determined force is applied to the finger operable means.

The finger operable means is in the form of two opposing levers 20, 21 each of which is pivotally connected to part of the housing 9 and is arranged to act upon a base portion 35 of the container 30 so as to urge the container 30 towards the nozzle 11 when the two levers 20, 21 are squeezed together by a user.

The fluid dispensing device 5 comprises of a plastic moulded body 6 and the fluid discharge device 8 and further comprises of a protective end cap (not shown) having an inner surface for engagement with the body 6 to protect the dispensing nozzle 11.

The body 6 is made from a plastic material such as polypropylene and defines the housing 9 and the dispensing nozzle 11 so that the housing 9 and the nozzle 11 are made as a single plastic component.

The housing 9 defines a cavity 10 formed by a front wall, a rear wall and first and second end walls 14a, 14b. The dispensing nozzle 11 is connected to one end of the housing 9, extends away from the housing 9 and has an external tapering form.

The discharge outlet from the compression pump is in the form of the tubular delivery tube 31 and a tubular guide in the form of an outlet tube 16 is formed within the nozzle 11 to align and locate the delivery tube 31 correctly with respect to the nozzle 11.

An annular abutment 17 is formed at the end of the outlet tube 16. The annular abutment 17 defines the entry to an orifice 15 through which fluid can flow in use and is arranged for abutment with an end of the delivery tube 31.

The fluid discharge device 8 has a longitudinal axis X-X and each of the levers 20, 21 has an abutment surface 22, 23 arranged at an angle θ to the longitudinal axis X-X of the fluid discharge device 8 for abutment against the base portion 35 of the container so as to convert a force applied to the levers 20, 21 substantially transversely to the longitudinal axis X-X of the fluid discharge device 8 into a force along the longitudinal axis X-X of the fluid discharge device 8.

The nozzle 11 has a longitudinal axis that is aligned with the longitudinal axis X-X of the fluid discharge device 8. This has the advantage that when the compression pump is actuated the force applied to the tubular delivery tube 31 is along the axis of the tubular delivery tube 31 and no bending or deflection of the delivery tube 31 will occur due to the applied force.

At least part of the surface of the base portion 35 of the container 30 is inclined at an angle with respect to the longitudinal axis X-X of the fluid discharge device 8 so as to form an inclined surface, the or each inclined surface being arranged to be acted upon by the levers 20, 21 so as to convert a force applied to the levers 20, 21 substantially transversely to the longitudinal axis X-X of the fluid discharge device 8 into a force along the longitudinal axis X-X of the fluid discharge device 8.

Although in the disclosed embodiment both the levers and the container have surfaces inclined to the longitudinal axis of the fluid discharge device this need not be the case. Only the container or the levers need have an inclined surface or some other arrangement to apply the force from the levers to the container could be used.

The base portion 35 of the container 30 has two inclined surfaces 37, 38 each arranged for co-operation with a respective one of the levers 20, 21.

However it will be appreciated that the inclined surface of the base portion of the container could be a conical, frusto-conical or part spherical surface.

The inclined surface 37 is arranged to co-operate with the abutment surface 22 and the inclined surface 38 is arranged to co-operate with the abutment surface 23.

The abutment surface 22 is formed by an edge of a web 24 formed as part of the lever 20 and the abutment surface 23 is formed by an edge of a web 25 formed as part of the lever 21.

In the arrangement shown in FIG. 2A, the pre-load means is interposed between the levers 20, 21 and the container and as shown is in the form of small step 28 formed near to the end of each abutment surface 22, 23. In the ready for use position this lies against a side of the container 30 at the juncture of the side of the container with the base portion 35. The purpose of this step 28 is to prevent the levers 20, 21 from moving the container 30 until more than a pre-determined force has been applied to the levers 20, 21.

The step 28 formed on each lever 20, 21 must be ridden over by the container 30 before the compression pump can be actuated. The step 28 is over-ridden when the pre-determined force is applied to each lever 20,21 and once this pre-determined force is exceeded the pressure being applied to the levers 20, 21 is such that the container 30 is very rapidly moved towards the nozzle 11. This prevents the levers 20, 21 being slowly squeezed together which will not produce a uniform spray and if done very slowly will merely cause the fluid to dribble out of the nozzle 11.

Figure 2B:
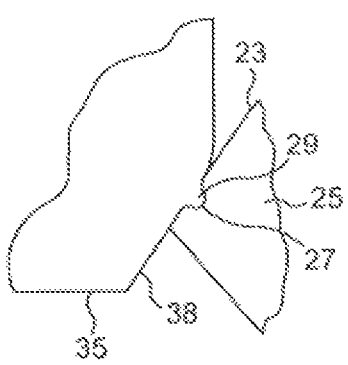
FIG. 2b is an enlarged view similar to that shown in FIG. 2a but showing an alternative pre-load means.

FIG. 2B shows an alternative arrangement in which the pre-load means comprises of a detent or protuberance 29 formed on the container 30 and complementary recess 27 formed on each lever 20,21. The size of the detent 29 is such that they are able to ride out of the recess 27 when the pre-determined force is applied to each lever 20, 21. It will be appreciated that in other alternatives, the recess could be formed in the container and the detent could be formed on the levers.

Each of the levers 20, 21 is pivotally connected to part of the housing 9 by a respective living hinge. In the embodiment shown each of the levers 20, 21 is pivotally connected to a respective one of the two side walls 14a, 14b by a respective living hinge 26 although other means of pivotal connection could be used.

The fluid discharge device 8 is in most respects conventional and will only be described briefly herein.

The fluid discharge device 8 has a hollow container 30 defining a reservoir containing several doses of the fluid to be dispensed and the compression pump that is attached to a neck 34 of the container 30.

The container 30 as shown is made from a translucent or transparent plastics material however it will be appreciate that it could be made from other translucent or transparent materials such as glass.

The compression pump includes a plunger (not shown) slidingly engaged within a pump casing that defines a chamber (not shown) sized to accommodate a single dose of fluid. The plunger is attached to the tubular delivery tube 31 that is arranged to extend from one end of the pump for co-operation with the outlet tube 16 of the dispensing nozzle 11. The plunger includes a piston (not shown) slidably supported in the chamber formed in the pump casing.

The fluid is discharged through a discharge channel defined by the tubular delivery tube 31 into the orifice 15 of the dispensing nozzle 11.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing is connected to the container 30 such that when the piston is moved by a return spring of the pump (not shown) into a start position a new dose of fluid is drawn into the cylinder via the suction inlet in the form of a pick-up tube from the container 30 ready for discharge.

Operation of the fluid dispensing device is as follows.

From the position shown in FIG. 1 in which the end portions of the abutment surfaces 22, 23 abut gently against the inclined surfaces 37, 38 of the container 30 and the container 30 is abutting with the steps 28 a user first grasps the fluid dispensing device 5 by the two levers 20, 21. Provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-load means formed in alternative embodiments, by the steps 28 of FIG. 2A or the detents/recesses 29, 27 arrangement of FIG. 2B.

If the user then squeezes the two levers 20, 21 together with increasing force the pre-determined force required to cause the container 30 to ride up over the steps 28 (or detents/recesses 29, 27) will be attained and the interaction of the abutment surfaces 22, 23 with the inclined surfaces 37, 38 will then cause the container 30 to be moved rapidly towards the nozzle 11 as indicated by the arrow 'M' on FIG. 3.

However, the abutment between the end of the delivery tube 31 and the annular abutment 17 will prevent movement of the delivery tube 31 in the same direction.

This effect of this is to cause the delivery tube 31 to push the plunger into the pump casing thereby moving the piston of the pump in the cylinder. This movement causes fluid to be expelled from the cylinder into the delivery tube 31. The fluid forced into the delivery tube is then transferred into the orifice 15 from where it is expelled as a fine spray into the body orifice.

Upon releasing the pressure applied to the levers 20, 21 the delivery tube 31 is urged out of the pump casing by the internal return spring and causes fluid to be drawn up the pick-up tube to re-fill the cylinder. The container 30 will then be allowed to move back into engagement with the steps 28 formed in the levers 20, 21 ready for the next actuation of the fluid dispensing device 5.

The actuating procedure can then be repeated until all of the fluid in the container has been used. However, only one or two doses of fluid are normally administered at a time.

When the container is empty a new fluid discharge device 8 is loaded into the housing 9 thereby restoring the fluid dispensing device 5 into a useable condition.

Figure 4:
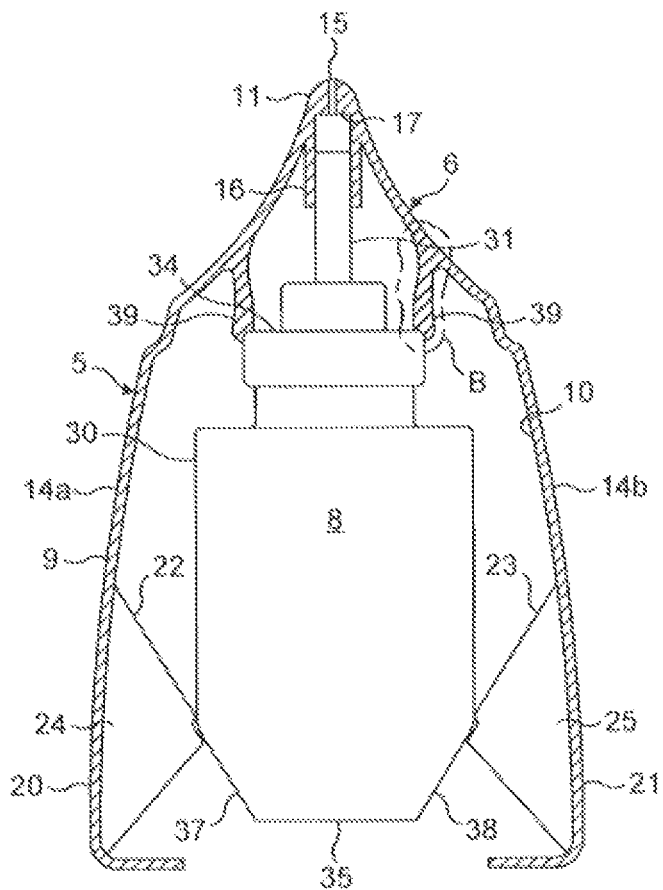
FIG. 4 is a cross-section similar to that shown in FIG. 1 but showing a pre-load means according to a second embodiment of the invention.
Figure 5:
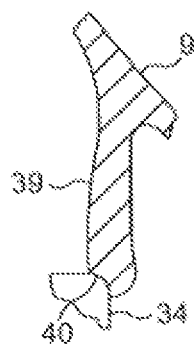
FIG. 5 is an enlarged view of the area indicated by 'B' on FIG. 4.

With reference to FIGS. 4 and 5 there is shown a fluid dispensing device that is in most respects identical to that previously described and for which the same reference numerals are used for like components.

The primary difference between the fluid dispensing means shown in FIGS. 1 to 3 and that shown in FIGS. 4 and 5 is that the fluid dispensing device 5 in FIGS. 4 and 5 uses a second embodiment of pre-load means in which the pre-load means 39, 40 is interposed between the housing 9 and the container 30.

The pre-load means comprises of two detents 39, 40 formed on the housing 9 for engagement with part of the container 30. The two detents 39, 40 are disengageable from the container 30 when the pre-determined force is applied to the finger operable means 20, 21 so as to allow the compression pump to be actuated.

Each of the detents is in the form of an arm 39, which extends downwardly from the housing 9 for engagement with a corner of the neck 34 of the container 30. A free end of each arm 39 has a step 40 formed therein, which prior to actuation is in abutting contact with the neck 34 of the container 30.

Operation of the fluid dispensing device is as follows.

From the position shown in FIG. 4 in which the end portions of the abutment surfaces 22, 23 abut gently against the inclined surfaces 37, 38 of the container 30 and the container 30 is abutting with the steps 40 a user first grasps the fluid dispensing device 5 by the two levers 20, 21. Provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-load means formed by the steps 40 and the arms 39 which prevent movement of the container towards the nozzle.

If the user then squeezes the two levers 20, 21 together with increasing force the arms 39 will begin to bow outwardly until when the pre-determined force is reached the neck 34 of the container 30 is able to disengaged itself from the steps 40 and the interaction of the abutment surfaces 22, 23 with the inclined surfaces 37, 38 will then cause the container 30 to be moved rapidly towards the nozzle 11.

However, as previously described the abutment between the end of the delivery tube 31 and the annular abutment 17 will prevent movement of the delivery tube 31 in the same direction thereby causing the compression pump to be actuated as the delivery tube 31 is pushed into the container 30. This movement causes fluid to be expelled from the container 30 into the delivery tube 31 and then into the orifice 15 from where it is expelled as a fine spray into the body orifice.

Upon releasing the pressure applied to the levers 20, 21 the delivery tube 31 is urged out of the container 30 causing fluid to re-fill the pump. The container 30 will then move back into engagement with the steps 40 formed in the arms 39 ready for the next actuation of the fluid dispensing device 5.

The actuating procedure can then be repeated until all of the fluid in the container has been used. However, only one or two dose volumes of fluid are normally administered at a time.

Figure 6:
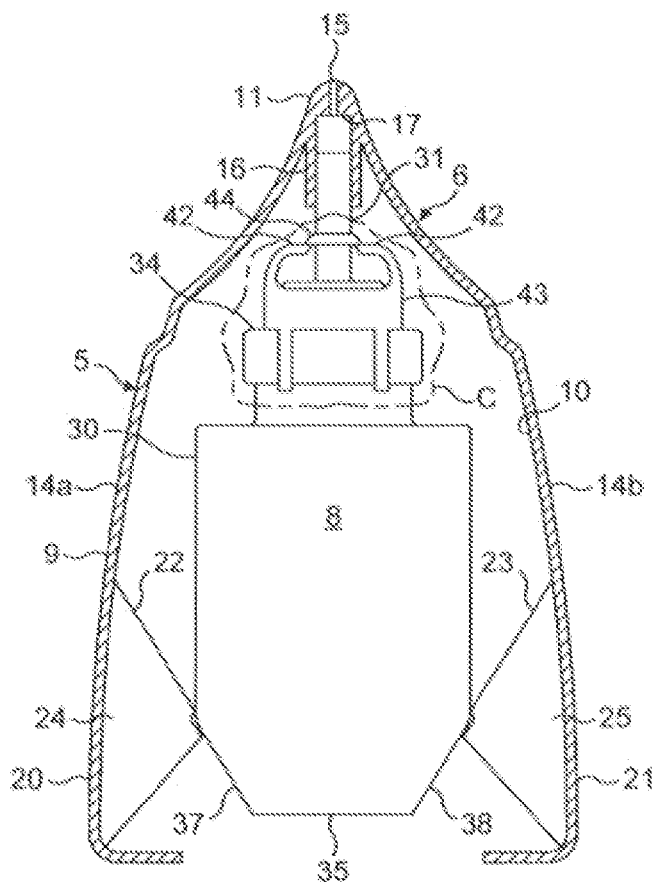
FIG. 6 is a cross-section similar to that shown in FIG. 1 but showing a pre-load means according to a third embodiment of the invention.
Figure 7:
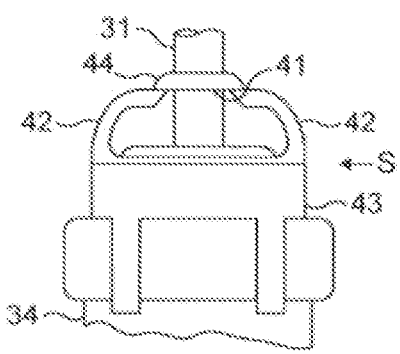
FIG. 7 is an enlarged view of the area indicated by 'C' on FIG. 6.
Figure 8:
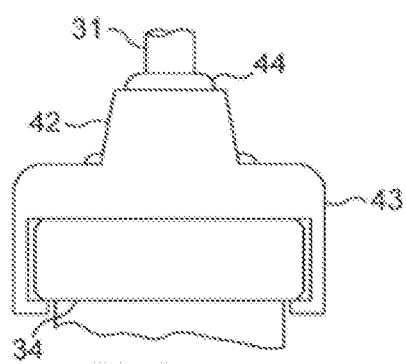
FIG. 8 is a side view in the direction of arrow 'S' on FIG. 7.

With reference to FIGS. 6 to 8 there is shown a fluid dispensing device that is in most respects identical to that previously described with respect to FIGS. 1 to 3 and for which the same reference numerals are used for like components.

The primary difference between the fluid dispensing means shown in FIGS. 1 to 3 and that shown in FIGS. 6 to 8 is that the fluid dispensing device 5 in FIGS. 6 to 8 uses a third embodiment of pre-load means in which the pre-load means 41, 42, 43 is interposed between the container 30 and the discharge tube 31.

This embodiment has the advantage that it can be used irrespective of the mechanism used to actuate the pump.

The pre-load means comprises of a step 41 formed on the discharge tube 31 and two latching members in the form of arms 42 attached by a collar 43 to the neck 34 of the container 30. The step 41 is formed by a rib 44 extending circumferentially around the discharge tube 31 and positioned such that when the pump is actuated the rib 44 does not prevent travel of the discharge tube 31 into the container 30.

The arrangement is such that, when the pre-determined force is applied to the finger operable means in the form of the levers 20, 21, the latching members or arms 42 are able to ride over the step 41 so as to allow the compression pump to be actuated but when a force below the pre-determined force is applied the interengagement of the arms 42 with the step 41 prevents the discharge tube 31 from moving into the container 30.

Operation of the fluid dispensing device is as previously described and provided that only a light pressure is applied to the levers 20, 21 no fluid will be discharged and the user is able to manoeuvre the dispensing nozzle 11 of the fluid dispensing device 5 into the body orifice into which fluid is required to be dispensed. This is because of the presence of the pre-load means formed by the step 41 and the arms 42 which prevent movement of the container 30 towards the nozzle 11.

If the user then squeezes the two levers 20, 21 together with increasing force the arms 42 will begin to bow until when the pre-determined force is reached the arms 42 are able to disengage themselves from the step 41 and the interaction of the abutment surfaces 22, 23 with the inclined surfaces 37, 38 will then cause the container 30 to be moved rapidly towards the nozzle 11.

This movement causes fluid to be expelled from the container 30 into the delivery tube 31 and then into the orifice 15 from where it is expelled as a fine spray into the body orifice.

Upon releasing the pressure applied to the levers 20, 21 the delivery tube 31 is urged out of the container 30 causing fluid to re-fill the pump. The container 30 will then move back allowing the arms 42 to re-engage with the step 41 ready for the next actuation of the fluid dispensing device 5.

The actuating procedure can then be repeated until all of the fluid in the container has been used. However, only one or two doses of fluid are normally administered at a time.

It will be appreciated that alternatively, the pre-load means may comprise of a recess formed on the discharge tube 31 and at least one latching member or arm attached to the container 30, the arrangement being such that, when the pre-determined force is applied to the finger operable means in the form of the levers 20, 21 the or each latching member is able to ride out of the recess so as to allow the compression pump to be actuated.

Figure 9:
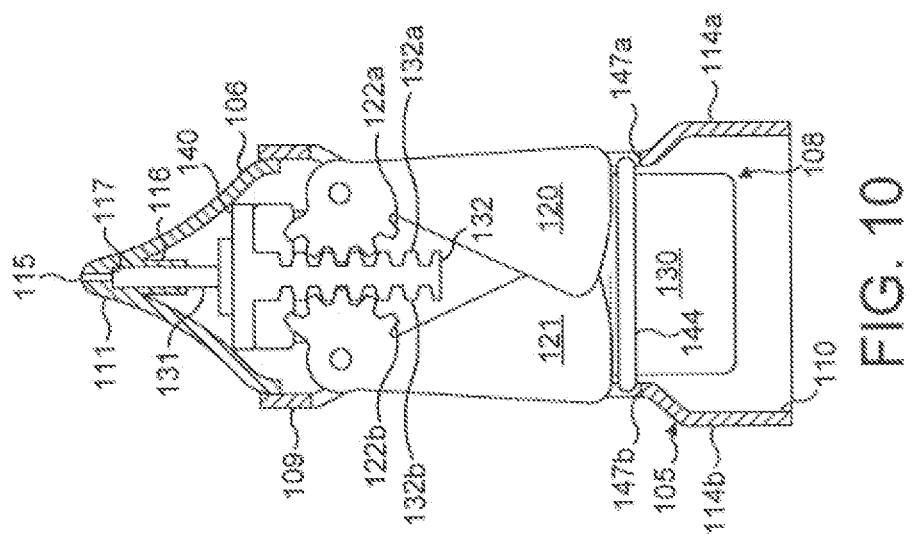
FIG. 9 is a cross-section of a fluid dispensing device having an alternative mechanism to actuate the fluid discharge device to that shown in FIG. 1 and having a pre-load means according to the second embodiment of the invention.
Figure 10:
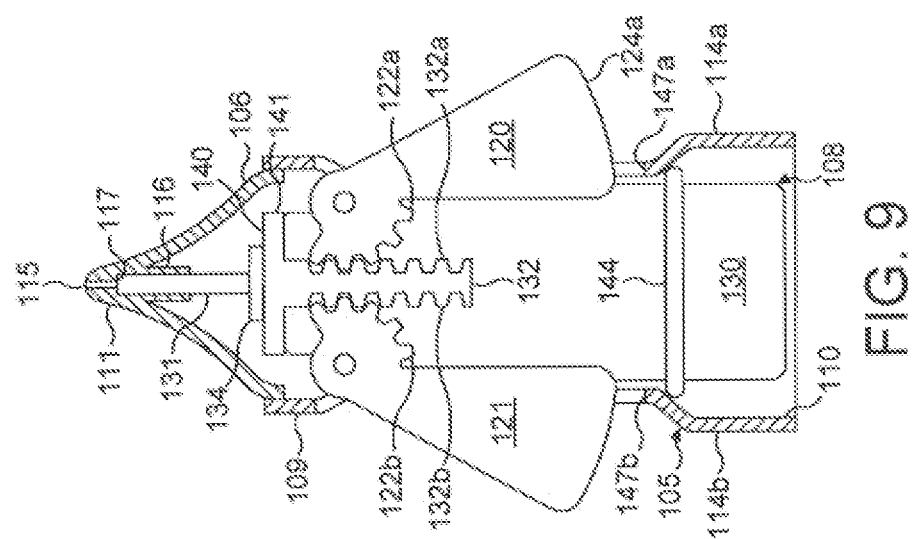
FIG. 10 is a cross-section as shown in FIG. 9 but showing the mechanism used to actuate the fluid discharge device in an actuated position.

With reference to FIGS. 9 and 10 there is shown a fluid dispensing device 105 which is in many respects similar to that previously described but instead of direct actuation of the fluid discharge device by the levers, the finger operable means in the form of two lever 120, 121 are used to apply a force to an actuating means 122a, 122b; 132, 132a, 132b used to move a container 130 towards a nozzle 111 so as to actuate the pump. For similar parts, corresponding reference numerals will be used to those previously used in respect of FIGS. 1 to 3

The actuating means 122a, 122b, 132, 132a, 132b is connected to a neck 134 of the container 30.

The fluid dispensing device 105 for spraying a fluid into a body cavity comprises a housing 109, a nozzle 111 for insertion into a body cavity and a fluid discharge device 108 moveably housed within the housing 109. The fluid discharge device 108 comprises of a container 130 for storing the fluid to be dispensed and a compression pump having a suction inlet located within the container 130 and a discharge outlet 131 at one end of the container 130 for transferring fluid from the pump to the nozzle 111.

A finger operable means in the form of the two levers 120, 121 is provided to apply a force to the container 130 to move the container 130 towards the nozzle 111 so as to actuate the pump.

The two opposing levers 120, 121 are pivotally supported within the housing 9 and are driveably connected to the container 130 by means of the actuating means so as to urge the container 130 towards the nozzle 111 when each lever 120, 121 is rotated by a user and in practice the two levers 120, 121 are squeezed together by a user. That is to say, squeezing the two levers 120, 121 together causes the container 130 to be moved towards the nozzle 111.

In more detail, the fluid dispensing device 105 comprises of a housing assembly and the fluid discharge device 108. The housing assembly comprises of the housing 109 for moveably supporting the fluid discharge device 108, a body 106 having the nozzle 111 extending therefrom and the two levers 120, 121 pivotally supported within the housing 109.

The body 106 and the nozzle 111 are made as a single part from a plastic material such as polypropylene and the body 106 is adapted at a lower end for engagement with an upper end of the housing 109. The body 106 and the housing 109 are fixed together by any suitable means.

The housing 109 defines a cavity 110 formed by a front wall, a rear wall and first and second end walls 114a, 114b.

The discharge outlet from the pump is in the form of a tubular delivery tube 131 and a tubular guide in the form of an outlet tube 116 is formed within the nozzle 111 to align and locate the delivery tube 131 correctly with respect to the nozzle 111.

An annular abutment 117 is formed at the end of the outlet tube 116. The annular abutment 117 defines the entry to an orifice 115 through which fluid can flow in use and is arranged for abutment with an end of the delivery tube 131.

The fluid discharge device 108 has a longitudinal axis co-incident with a longitudinal axis of the container 130 and a longitudinal axis of the tubular delivery tube 131. The nozzle 111 has a longitudinal axis which is aligned with the longitudinal axis of the fluid discharge device 108 so that when the pump is actuated the force applied to the tubular delivery tube 131 is along the longitudinal axis of the tubular delivery tube 131 and no bending or deflection of the delivery tube 131 will occur due to the applied force.

Each of the first and second levers 120, 121 is driveably connected to the container 130 near to said one end of the container 130 where the container terminates in a neck 134.

To form the driveable connection each of the first and second levers 120,121 has a pair of toothed portions 122a, 122b for engagement with a respective toothed rack 132 attached to the container 130 and in particular to the neck portion 134 of the container 130. Each of the racks 132 is arranged so as to extend parallel to the longitudinal axis of the container 130.

Each of toothed racks 132 has two sets of opposed teeth, a first set of teeth 132a for engagement with the first lever 120 and a second set of teeth 132b for engagement with the second lever 121.

The neck portion 134 of the container 130 has a cylindrical outer surface and the two toothed racks 132 are arranged on opposite sides of the neck portion 134 so that the two toothed racks 132 are arranged diametrically opposite with respect to the neck portion 134.

Each of the toothed racks 132 is connected to a collar 140 used to attach the toothed racks 132 to the neck portion 134 of the container 130.

It will be appreciated that the levers 120, 121 can be pivotally attached to the housing 109 in any convenient manner or that each lever 120, 121 could be pivotally supported within the housing 109 by a pivotal connection between each lever 120, 121 and the body member 106.

The fluid discharge device 108 is as has previously been described and will not be described again other than to mention that actuation of the pump occurs when the discharge tube 131 is pushed into the container 130.

The fluid dispensing device 105 is fitted with a pre-load means according to the second embodiment of the invention, that is to say, the pre-load means 144 is interposed between the housing 109 and the container 130.

The pre-load means comprises of a detent in the form of a circumferentially extending rib 144 formed on the container 130 for engagement with part of the housing 109. The rib 144 is arranged for engagement with two inwardly extending fingers 147a, 147b formed in the side walls 114a, 114b of the housing 109. Each of the fingers 147a, 147b is attached to the respective side wall 114a, 114b be a living hinge such that movement of the fingers 147a, 147b towards the nozzle is prevented but pivoting of the fingers 147a, 147b relative to the housing 109 is possible when they are urged away from the nozzle 111. This provides a resistance to passage of the rib 144 if the container 130 is moved towards the nozzle 111 but offers little to resistance to passage of the rib 144 if the container is moving away from the nozzle 111.

Therefore, the detent or rib 144 is disengageable from the housing 109 or more specifically the fingers 147a, 147b when a pre-determined force is applied to the finger operable means 120, 121 so as to allow the compression pump to be actuated.

Operation of the fluid discharge device 105 is as follows.

First, a user must grasp the fluid dispensing device 105 by the two levers 120, 121, provided that only a light pressure is applied to the levers 120, 121 no fluid will be discharged due to the interaction between the rib 144 and the two fingers 147a, 147b and the user is able to manoeuvre the dispensing nozzle 111 of the fluid dispensing device 105 into the body orifice into which fluid is required to be dispensed. If the user then squeezes the two levers 120, 121 together with increasing force eventually a pre-determined force will be reached at which point the rib 144 is able to disengage with the housing 109 by riding over the fingers 147a, 147b and the interaction of the toothed portions 22a, 22b with the racks 132 will then cause the container 130 to be moved rapidly towards the nozzle 111.

However, because the end of the delivery tube 131 is in abutting contact with the annular abutment 117, the delivery tube 131 cannot move in the same direction. The effect of this is to cause the delivery tube 131 to be pushed into the container causing fluid to be expelled from the delivery tube 131 into the orifice 115 from where it is expelled as a fine spray into the body orifice.

At the end of the delivery stage when the fluid discharge device has been discharged the two levers 120, 121 have been rotated so that they lie close to or flush with the side walls 114a, 114b as shown in FIG. 10.

Upon releasing the pressure applied to the levers 120, 121 the delivery tube 131 is urged out of the pump casing by an internal return spring and causes fluid to be drawn up to re-fill the pump.

The actuating procedure can then be repeated until all of the fluid in the container has been used. However, only one or two volumes of fluid are normally administered at a time.

When the container is empty a new fluid discharge device 108 is loaded into the housing 109 thereby restoring the fluid dispensing device 105 into a useable condition.

Figure 11:
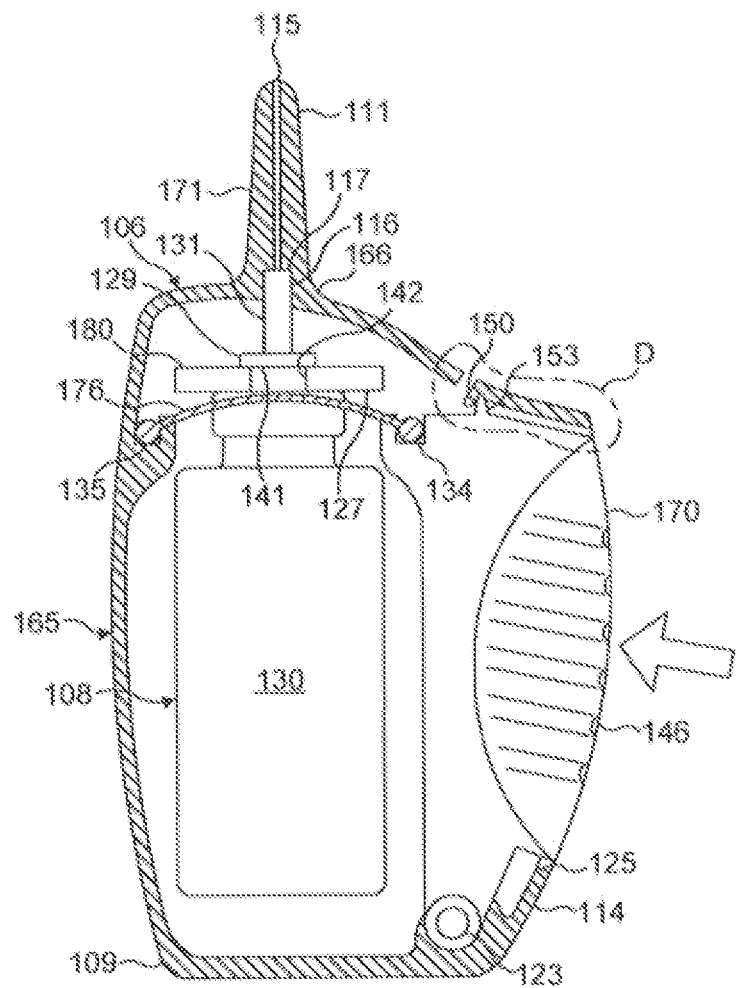
FIG. 11 is a cross-section of a fluid dispensing device having an alternative mechanism to actuate the fluid discharge device to that shown in FIG. 1 and having a pre-load means according to a fourth embodiment of the invention.
Figure 12:
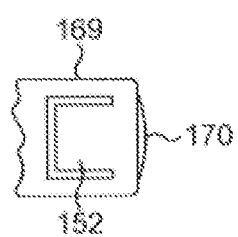
FIG. 12 is a plan view of the area indicated by 'D' on FIG. 11.

With reference to FIGS. 11 and 12 there is shown a fluid dispensing device 165 which is in many respects similar to that shown in FIGS. 1 to 3, but in which a single lever 170 is used to apply a force to an actuating means 176 used to move a container 130 towards a nozzle 111 and actuate a compression pump. The lever 170 is pivotally supported at a lower end within a housing 109 and the actuating means 176 is connected to a neck 129 of the container 130 by a collar 140.

The fluid dispensing device 165 is fitted with a fourth embodiment of a pre-load means in which the pre-load means 150, 152, 153 is interposed between the housing 109 and the lever 170.

The pre-load means comprises of a detent in the form of a tooth 150 formed on the housing 109 for engagement with the lever 170. The tooth 150 is formed at the end of an arm 152 formed as an integral part of the housing 109 and the lever 170 has a complementary rib 153 formed thereon for engagement with the tooth 150.

The detent or tooth 150 is disengageable from the rib 153 on the lever 170 when a pre-determined force is applied to the lever 170 so as to allow the compression pump to be actuated.

In more detail the fluid dispensing device 165 comprises of a body structure including the housing 109, the nozzle 111 extending out from an upper end of the housing 109 for insertion into a body cavity and a fluid discharge device 108 moveably housed within the housing 109.

The fluid discharge device 108 comprises of the container 130 for storing the fluid to be dispensed and the compression pump having a suction inlet located within the container 130 and a discharge outlet 131 for transferring fluid from the pump to the nozzle 111.

The lever 170 is pivotally supported at a lower end within the housing 109 and the actuating means is connected to the neck 129 of the container 130 by a collar 140 engaged with the neck 129 of the container 130.

The body structure comprises of a two-part plastic housing 109 and a plastic body member 106 both of which are moulded from a suitable plastic material such as polypropylene. The nozzle 111 is formed as an integral part of the body member 106 and the body member 106 is fastened to the housing 109 so that the nozzle 111 projects from the upper end of the housing 109.

The housing 109 has an aperture formed in a side wall 114 from which, in use, a part of the lever 170 projects. The part of the lever 170 that projects from the aperture is a ribbed finger grip 146.

The discharge outlet from the pump is in the form of a tubular delivery tube 131 and a tubular guide in the form of an outlet tube 116 is formed within the nozzle 111 to align and locate the delivery tube 131 correctly with respect to the nozzle 111.

An annular abutment 117 is formed at the end of the outlet tube 116. The annular abutment 117 defines the entry to an orifice 115 through which fluid can flow in use and is arranged for abutment with an end of the delivery tube 131.

The fluid discharge device 108 is in most respects conventional and is as previously described herein.

The collar 140 is connected to the neck 129 of the container 130 by a snap connection in which the neck 129 has a groove 141 into which the collar 140 is snap fitted. The collar 140 has a slit 142 in one side that allows it to be pushed onto the neck 129 and engage with the groove 141.

The actuating means is a resilient flexible member in the form of a leaf spring 176 connected to an upper end of the lever 170 so as to hold the resilient flexible member 176 in an upwardly bowed state. However, it will be appreciated that more than one resilient flexible member could be used if required.

The lower end of the lever 170 is pivotally connected to the housing 109 by means of a pivot pin 123.

The resilient flexible member 176 is operably connected to the neck 129 of the container 130 by abutment of an upper surface of the resilient flexible member 176 against a lower surface 127 of the collar 140, which is attached to the neck 129 of the container 130.

A stop means 125 is provided to limit rotational movement of the lever 170 away from the container 130 so as to maintain the resilient flexible member 176 in a bowed state. The stop means 125 takes the form of one edge of the aperture through which the lever 170 projects.

The resilient flexible member 176 is connected at one end to the upper end of the lever 170 by engagement with a groove 134 formed in the lever 170 and is connected at an opposite end to part of the body structure of the fluid dispensing device 165 in the form of the housing 109 which has a groove 135 formed therein with which the resilient flexible member 124 is engaged.

It will be appreciated that if removed from the fluid dispensing device 165 the resilient flexible member will return to a flat planar shape as it undergoes no plastic deformation during use but only elastic deformation.

The stop 125 is positioned such that when the lever 120 is displaced fully from the container 130 so as to rest against the stop 125 the linear distance between the upper end of the lever 120 and the position of connection of the resilient flexible member 176 to the housing 109 is less than the un-bowed length of the resilient flexible member 176. This ensures that the flexible member never returns to a flat shape. This is important because the resilient flexible member must be bowed upwardly to function correctly and if it were to be fully released there is a possibility that upon re-applying a load to it would bow downwardly.

When the lever 120 is moved towards the container 130 so as to cause the container 130 to be moved towards the nozzle 111, the radius of curvature of the bowed resilient flexible member 176 is reduced and the collar 140 is moved upwardly thereby causing actuation of the pump.

Operation of the fluid dispensing device 165 is as follows.

After inserting a fluid discharge device 108 into the housing 109 the fluid dispensing device is ready for use and the lever 170 will be resting against the end stop 125.

To use the fluid dispensing device 165 a user must first grasp the fluid dispensing device 165 so that contact is made with the lever 170 and in particular with the ribbed finger grip 146.

Provided that only a light pressure is applied to the lever 170 no fluid will be discharged and the user is able to manoeuvre the dispensing nozzle 111 of the fluid dispensing device 165 into a body orifice such as a nasal cavity into which fluid is required to be dispensed. This is because of the presence of the pre-load means and in particular because the tooth 150 is abutting with the rib 153.

If the user then exerts more force upon the lever 170 the arm 152 will begin to bend and when the force applied to the lever 170 reaches a predetermined magnitude the tooth 150 is able to ride over or become detached from the rib 153 allow the lever 170 to move freely and the interaction of the resilient flexible member 176 upon the collar 140 will then cause the container 130 to be moved rapidly towards the nozzle 111.

This causes the delivery tube 131 to be pushed into the container thereby actuating the pump.

Upon releasing the pressure applied to the lever 170, the resilient flexible member 176 will try to assume is least deformed state and so will urge the lever 170 back upon its stop 125 as soon as the force is removed from the lever 170 allowing the tooth 150 to re-engage with the rib 153.

The actuating procedure can then be repeated until all of the fluid in the container has been used. However, only one or two doses of fluid are normally administered at a time.

When the container 130 is empty a new fluid discharge device 108 is loaded into the body member 106 thereby restoring the fluid dispensing device 165 into a useable condition.

Figure 13:
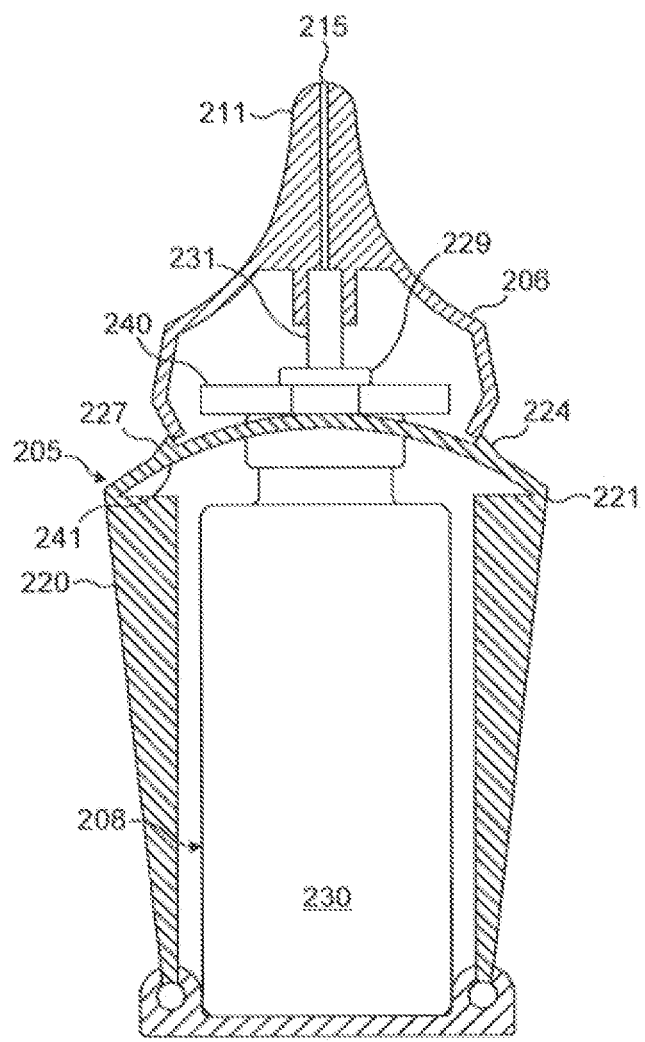
FIG. 13 is a cross-section of a fluid dispensing device having an alternative mechanism to actuate the fluid discharge device to that shown in FIG. 1 and having a pre-load means according to a fifth embodiment of the invention.
Figure 16:
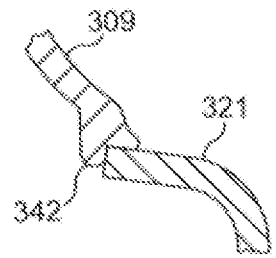
FIG. 16 is an enlarged cross-section of the area indicated by 'E' on FIG. 17.
Figure 17:
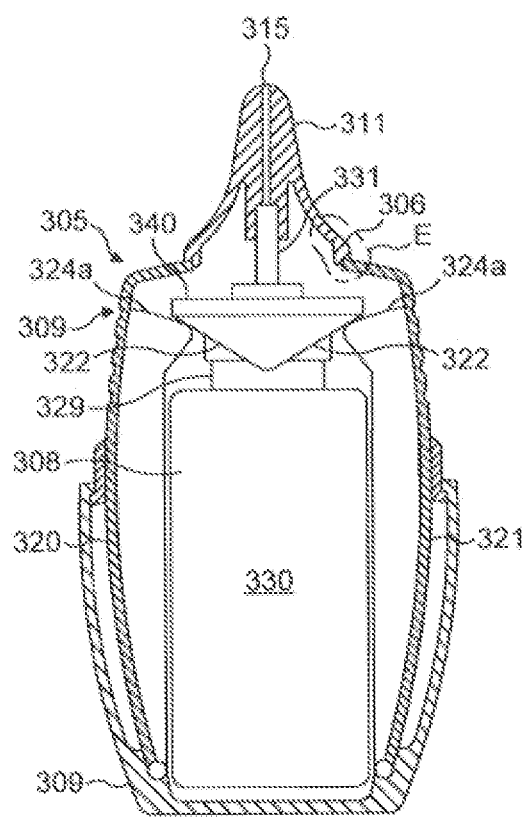
FIG. 17 is a cross-section of a fluid dispensing device shown in FIG. 14.

With particular reference to FIG. 13 there is shown a fluid dispensing device 205 which is in many respects similar to that described with respect to FIG. 11 but in which two levers 220, 221 pivotally supported at their lower ends are used to move a container 230 forming part of a discharge device 208 housed within a housing 206 by means of an actuating means in the form of a flexible member 241 which as shown is formed as a single part with the two levers 220, 221 but all three parts could be made as separate components.

The flexible member 242 is arranged to act against a collar 240 connected to a neck 229 of the container 230 so that when the two levers are squeezed together the flexible member 241 urges the container towards a nozzle 211 extending from one end of the housing 206. The movement of the container 230 towards the nozzle 211 causes relative movement between the container 230 and a discharge tube 231 connected to a pump housed within the container 230 thereby actuating the pump and causing fluid to be urged out through the discharge tube 231 into an orifice 215 formed in the nozzle 211 from whence it is dispensed as fine spray.

The fluid dispensing device 205 is fitted with a fifth embodiment of a pre-load means in which the pre-load means is interposed between the actuating means 241 and the housing 206.

The pre-load means comprises of two detents 224, 227 formed on part of the actuating means and in this case on an upper surface of the flexible member 241 for engagement with part of the housing. As can be seen, each of the detents 224, 227 is located such that when the levers 220, 221 are in a rest position they abut lightly against an adjacent outer surface of the housing 206.

When a small force is applied to the two levers 220, 221 the pump is not actuated because the detents 224, 227 prevent the flexible member from moving but when a force of a pre-determined magnitude is applied to the levers 220, 221 it is sufficient to cause the detents 224, 227 to disengage from the housing so as to allow the compression pump to be actuated. Because of the presence of the detents 224, 227 it is ensured that the container 230 is not moved until sufficient force is applied to the levers 220, 221 to cause rapid movement of the container 230 towards the nozzle 211 and guarantee that an effective spray is produced.

It will be appreciated that alternatively, the pre-load means could comprise of at least one detent formed on part of the housing for engagement with a complementary recess formed on part of the actuating means. In which case, each detent would be disengageable from its respective recess when the pre-determined force is applied to each lever so as to allow the compression pump to be actuated.

With reference to FIGS. 14 to 17 there is shown a fluid dispensing device 305 that is in many respects similar to those previously described.

The fluid dispensing device 305 comprises of a body 306 forming a nozzle 311 and a housing 309. A fluid discharge device 308 is housed within the housing 309. The fluid discharge device 308 comprises of a container 330 in which is fitted a compression pump (not shown) and a discharge tube 331 extending from one end of the container 330 for abutment against the nozzle 311. When the discharge tube 331 is moved into the container 330 the pump is actuated and fluid is urged out of the discharge tube 331 into an orifice 315 in the nozzle from whence it is emitted as a fine spray.

There is provided a finger operable means in the form of two opposing levers 320, 321 each of which is pivotally supported near a lower end of the housing 309 and is arranged to act upon an actuating means 322 so as to urge the container 330 towards the nozzle 311 when the two levers 320, 321 are squeezed together.

The actuating means is in the form of two inclined ramps 322 each of which is arranged to cooperate with a complementary inclined surface 324a formed on a respective one of the two levers 320, 321. The two ramps 322 are connected to the container 330 by means of a collar 340 that is engaged with a neck 329 of the container.

Movement of the two levers 320, 321 towards each other causes the inclined surfaces 324a to ride up the ramps 322 thereby urging the container towards the nozzle 311.

The fluid dispensing device 305 is fitted with a pre-load means interposed between the housing 309 and the levers 320, 321.

The pre-load means comprises of a detent or step 342 formed on each side of the housing 309 for engagement with an end face of each lever 320, 321.

Movement of the levers 320, 321 is prevented by their engagement with the steps 342 until a pre-determined force is applied to them at which point the force applied is sufficient to cause the ends of the levers 320, 321 to ride out of the steps 342 and permit free movement of the levers 320, 321 towards the container 330 thereby causing actuation of the pump. In this way it is guaranteed that the pump will not be actuated until sufficient force is being applied to cause a rapid movement of the discharge tube 331 into the container 330.

Figure 18:
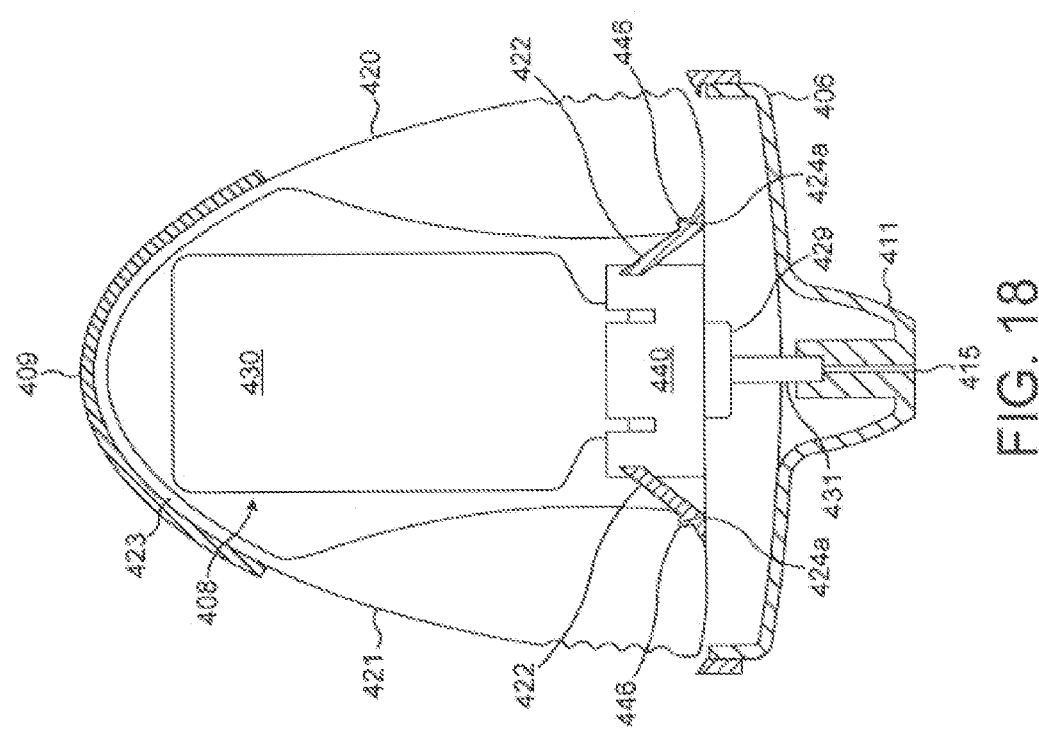
FIG. 18 is a cross-section of a fluid dispensing device having an alternative mechanism to actuate the fluid discharge device to that shown in FIG. 1 and having a pre-load means according to a sixth embodiment of the invention.

With reference to FIG. 18 there is shown a fluid dispensing device 405 that is in many respects similar to that previously described with reference to FIGS. 14 to 17 but in which the pre-load means is interposed between each lever 420, 421 and the respective actuating means 422.

The fluid dispensing device 405 comprises of a body 406 forming a nozzle 411 and a housing 409. A fluid discharge device 408 is housed within the housing 409. The fluid discharge device 408 comprises of a container 430 in which is fitted a compression pump (not shown) and a discharge tube 431 extending from one end of the container 430 for abutment against the nozzle 411. When the discharge tube 431 is moved into the container 430 the pump is actuated and fluid is urged out of the discharge tube 431 into an orifice 415 in the nozzle from whence it is emitted as a fine spray.

There is provided a finger operable means in the form of the two opposing levers 420, 421 each of which is pivotally supported near a lower end of the housing 409 by being connected together by a flexible strap 423 and is arranged to act upon the actuating means 422 so as to urge the container 430 towards the nozzle 411 when the two levers 420, 421 are squeezed together.

The actuating means is in the form of two inclined ramps 422 each of which is arranged to cooperate with a complementary curved surface formed on a respective one of the two levers 420, 421. The two ramps 422 are connected to the container 430 by means of a collar 440, which is engaged with a neck 429 of the container 430. The ramps 422 and the collar 440 may both be of a plastics material, and further may be integrally formed, e.g. by moulding.

Movement of the two levers 420, 421 towards each other causes the curved portions of the levers 420, 421 to ride up the ramps 422 thereby urging the container 430 towards the nozzle 411.

The fluid dispensing device 405 is fitted with a pre-load means interposed between the actuating device 422 and the levers 420, 421.

The pre-load means comprises of a detent 424a formed on each actuating means in the form of an inclined ramp 422 for engagement with a recess 446 formed in each lever 420,421.

Each of the detents 424a is disengageable from its respective complementary recess 446 when a pre-determined force is applied to the respective lever 420, 421 so as to allow the compression pump to be actuated.

Operation of the fluid dispensing device is as previously described when a user grasps the two levers 420, 421 with less than the pre-determined force movement of the levers 420, 421 is prevented by the engagement of the detents 424a with the recesses 446 but as soon as a force equal to or greater than the pre-determined force is applied to the levers 420, 421 then the detents 424a are able to disengage or ride out of the recesses 446 and the two levers 420, 421 will move rapidly together thereby actuating the compression pump.

This ensures that the pump is only actuated when sufficient force is being applied to guarantee the production of an effective spray.

It will be appreciated that the pre-load means could alternatively comprise of at least one detent formed on each lever for engagement with a respective recess formed on part of the actuating means. In which case, each detent would be disengageable from its respective complementary recess when the pre-determined force is applied to the lever so as to allow the compression pump to be actuated.

Figure 19:
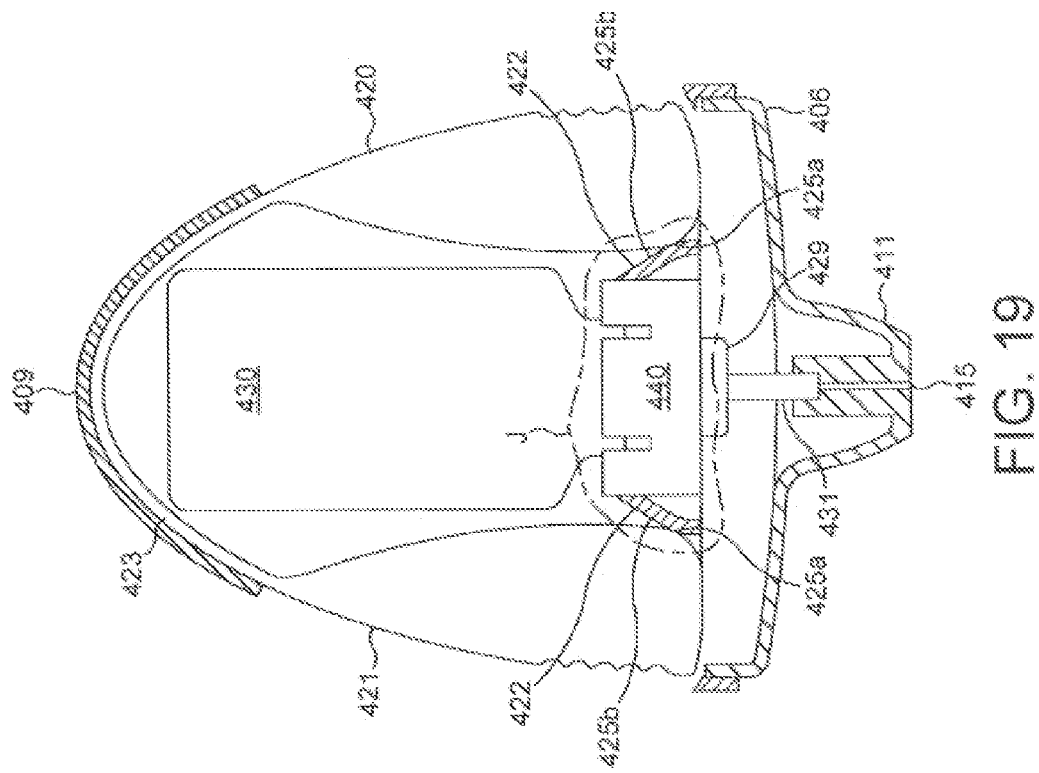
FIG. 19 is a cross-section that is similar to that shown in FIG. 18 but showing an alternative pre-load means according to the sixth embodiment of the invention.

With reference to FIG. 19 there is shown a fluid dispensing device 405 that is in many respects similar to that previously described with reference to FIG. 18 but in which an alternative form of pre-load means is interposed between each lever 420, 421 and the respective actuating means 422. The same reference numerals are used for like parts and the construction of the fluid dispensing device 405 will not be described further except so far as it relates to the pre-load means.

Figure 19A:
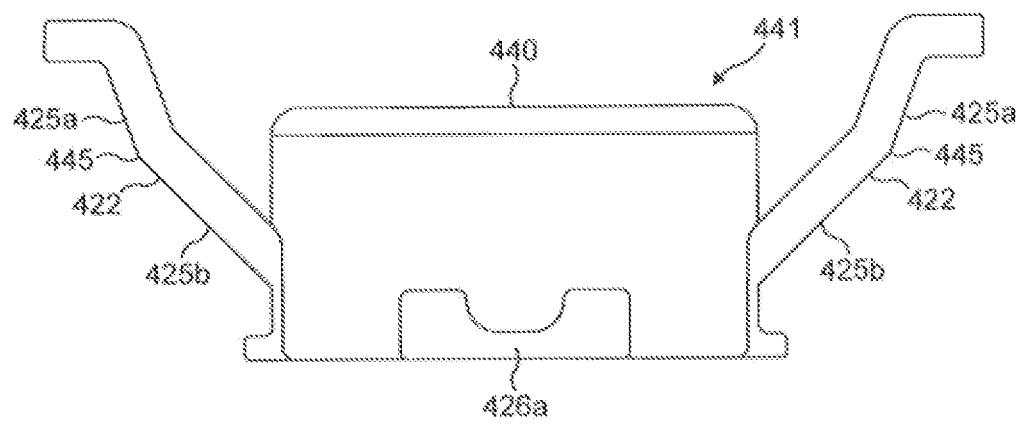
FIG. 19a is an enlarged side view of the collar occupying area indicated by 'J' on FIG. 19.
Figure 19B:
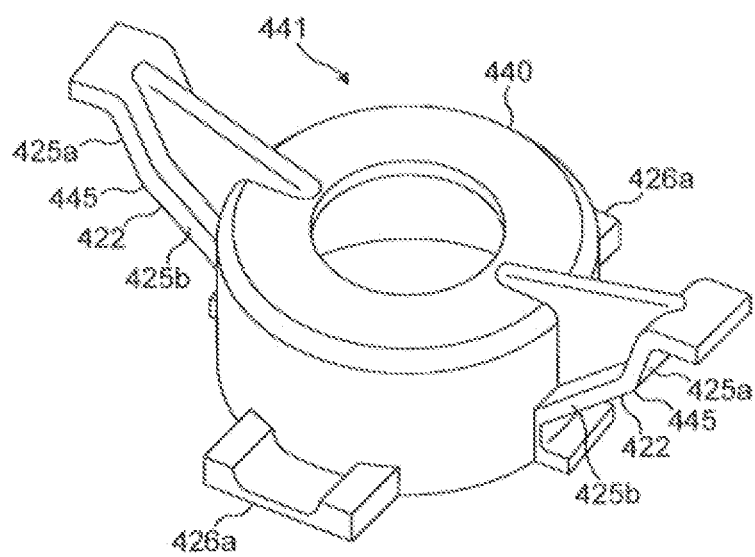

The features of the actuating device 422 may be better understood having regard to FIGS. 19a and 19b, which show side and perspective views thereof.

The pre-load means comprises of an actuating device 441 having a collar 440 for receipt by neck 429 of the container 430. The actuating device 441 is provided on opposing sides with ramps 422, each having a variable mechanical ratio such that until a pre-determined force is applied to each lever 420, 421 no significant force is transferred to the container 430.

This is achieved by having a first portion 425a of each ramp 422 inclined at a lesser angle (e.g. approx 20°) to a longitudinal (i.e. vertical, as shown) axis of the fluid discharge device 408 than is the remaining length 425b (e.g. angle approx. 45°) of each ramp 422. Therefore when a force is initially applied to each lever 420, 421 it is applied substantially normal to the longitudinal axis of the fluid discharge device 408 and virtually no force is converted into a force along the longitudinal axis of the fluid discharge device 408 and so the static friction between the first portion 425a of each ramp 422 and the cooperating lever 420, 421 is sufficient to maintain the levers 420, 421 stationary. However, when a pre-determined load is applied to each lever 420, 421 the static friction is overcome and each lever 420, 421 is able to start moving along the first portion 425a of the cooperating ramp 422. When each lever 420, 421 reaches the end of the first portion 425a, the change in inclination of the surface with which the lever 420, 421 is cooperating in combination with the magnitude of the force being applied ensures that each lever 420, 421 suddenly slides rapidly along the second portion 425b of the cooperating ramp 422 causing the container 430 to be moved rapidly towards the nozzle 411 to actuate the compression pump.

This ensures that the pump is only actuated when sufficient force is being applied to guarantee the production of an effective spray.

As visible in FIGS. 19a and 19b, the actuating device 441 is also provided on opposing sides of the collar 440 with guide rails 426a, each perpendicularly arranged with respect to both ramps 422. The guide rails 426a interact with mating guides (not visible) on the housing 409 to ensure uniform longitudinal movement of the container 430 during actuation.

It will be appreciated that the profile defined by the ramps 422 of the actuating device 441 of FIGS. 19a and 19b is that of an initial linear 'high force' (i.e. high gradient) profile 425a (defining the pre-load force, to be overcome) and a subsequent linear 'lower force' (i.e. lower gradient) profile 425b with a relatively sharp break point 445 therebetween.

Conveniently, the actuating device may be made from a plastics material, for instance by moulding.

Figure 19C:
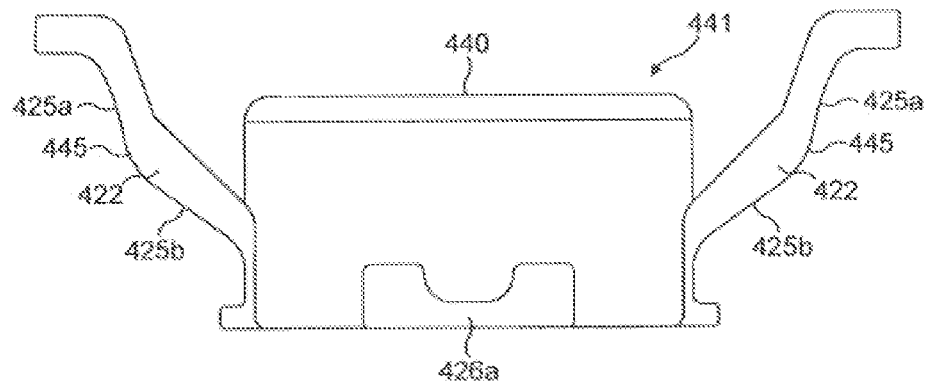
FIG. 19c is an enlarged side view of a first alternative form of the collar occupying area indicated by 'J' on FIG. 19.
Figure 19D:
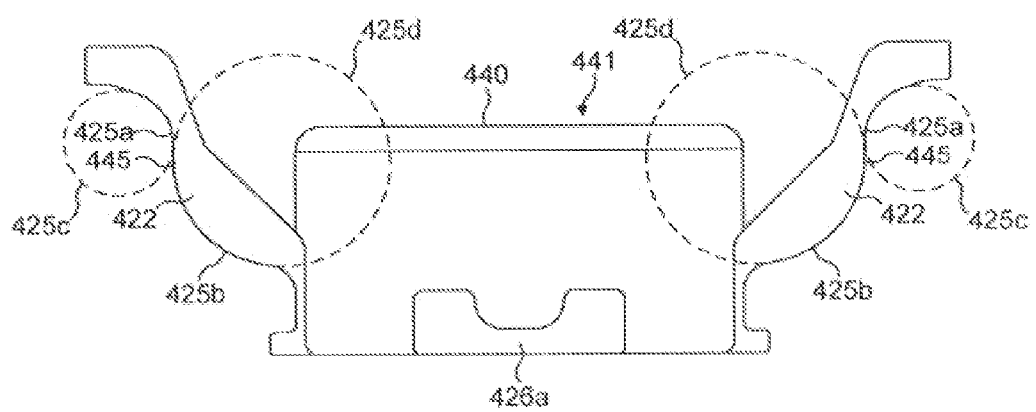
FIG. 19d is an enlarged side view of a second alternative form of the collar occupying area indicated by 'J' on FIG. 19.

Variations of ramp profiles can be envisaged, as for example, shown in FIGS. 19c and 19d.

The profile defined by the ramps 422 of the actuating device 441 of FIG. 19c is that of an initial curved 'high force' (i.e. high gradient) profile 425a (defining the pre-load force, to be overcome) and a subsequent curved 'lower force' (i.e. lower gradient) profile 425b with a relatively smooth/gradual break point 445 therebetween.

The profile defined by the ramps 422 of the actuating device 441 of FIG. 19d is that of an initial part-circle 'high force' (i.e. high gradient) profile 425a (defining the pre-load force, to be overcome) and a subsequent part-circle 'lower force' (i.e. lower gradient) profile 425b with a relatively smooth/gradual break point 445 therebetween. In more detail, the 'high force' 425a and 'low force' 425b profiles may be seen to have profile forms as would be defined by overlapping circles 425c, 425d of different radii and different centre points (illustrated schematically, in outline only).

Figure 41A:
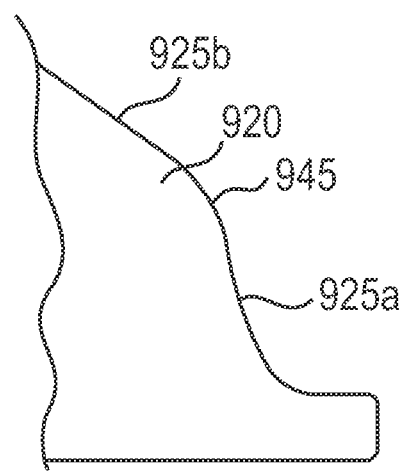
FIG. 41 a is a view of an embodiment of a lever of the present invention having a dual gradient profile.
Figure 41B:
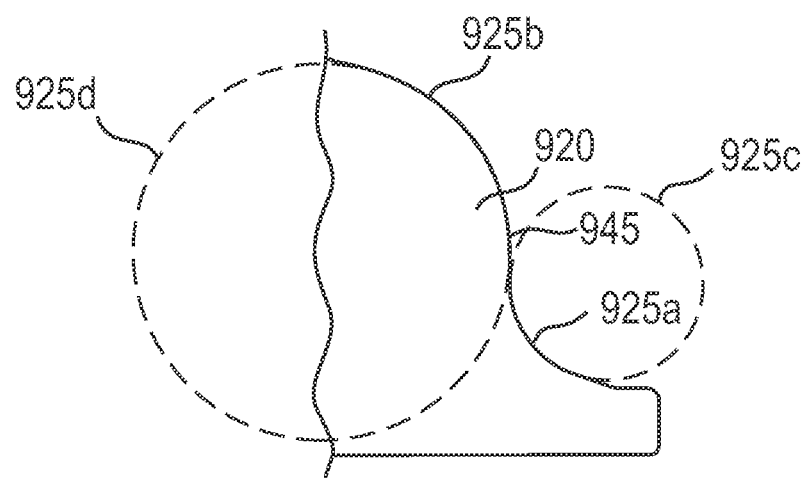

Whilst FIGS. 19a to 19d have shown embodiments in which dual gradient profiles 425a, 425b are provided to ramps 422 on collar 440 that interact with a levers 420, 421, it may be appreciated that in variations thereof suitably configured dual-gradient profiles are provided to the levers 420, 421 for interaction with simple follower elements on ramps 422 of the collar 440. In this regard, FIGS. 41a and 41b show a lever 920 provided with a dual-gradient profile which respectively corresponds to that provided to the collar 440 in FIGS. 19c and 19d, with like features being designated with like reference numerals. (e.g., 925a corresponding to 425a, 925b to 425b, 925c to 425c, 925d to 425d, and 945 to 445).

With reference to FIGS. 20 and 21 there is shown a fluid dispensing means that is in most respects identical to that previously described with respect to FIGS. 18 and 19 and for which the same reference numerals are used for identical parts. The only difference between the fluid dispensing device 405 shown in FIGS. 20 and 21 and those shown in FIGS. 18 and 19 is the arrangement of the pre-load means, which in this case is interposed between each of the levers 420, 421 and the housing 409. In addition, an end cap 407 is shown fitted in FIGS. 20 and 21.

The pre-load means comprises of two detents or protrusions 428 formed on each of the levers 420, 421 for engagement with a bevelled surface 427 formed around the periphery of an aperture in the housing 409 through the respective lever 420, 421 projects.

When a light force is applied to the two levers 420, 421 they are prevented from moving into the housing by the abutment of the detents 428 with the bevelled surfaces 427. When the force applied to each lever 420, 421 reaches a pre-determined magnitude it is sufficient to deflect the side walls of the levers 420, 421 inwardly so allowing the detents 428 to ride across the bevelled surfaces 427 into the housing 409. A soon as the detents have passed over the bevelled surfaces 427 the levers 420, 421 are free to move towards the container 430 housed within the housing 409 so as to actuate the pump. Once again, this ensures that a reliable spray is produced.

When the force is released from the levers 420, 421 they are moved back towards their start positions but require the application of a small outward force in order to re-engage the detents 428 with the bevelled surfaces 427.

Figure 22:
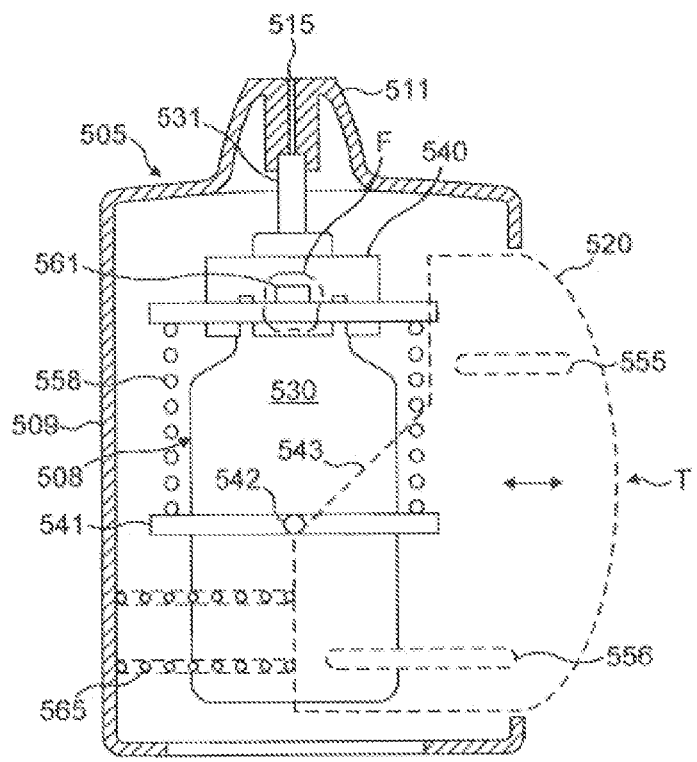
FIG. 22 is a cross-section of a fluid dispensing device having an alternative mechanism to actuate the fluid discharge device to that shown in FIG. 1 and having a pre-load means according to the second embodiment of the invention.
Figure 23:
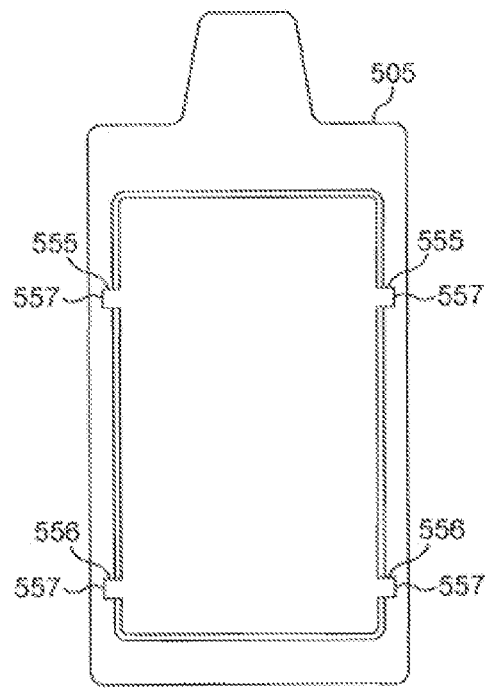
FIG. 23 is a side view in the direction of arrow 'T' on FIG. 22.
Figure 24:
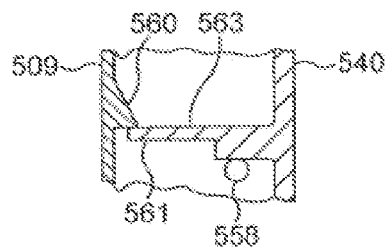
FIG. 24 is cross-section of the area indicated by 'F' on FIG. 22.

With particular reference to FIGS. 22 to 24 there is shown a fluid dispensing device 505 having a housing 509 for housing a fluid discharge device 508. The housing has a nozzle 511 extending out from one end for engagement with a body orifice such as a nasal cavity.

The fluid discharge device is conventional in nature and as is previously described having a container 530 for the fluid to be dispensed, a compression pump fixed within the container 530 and a discharge tube 531 extending out from the pump to deliver fluid to an orifice 515 formed in the nozzle 511. As previously described the pump is actuated by pushing the discharge tube 531 into the pump, which is achieved by moving the container 530 towards the nozzle 511.

A finger operable means is provided to move the container 530, the finger operable means is in the form of a lever 520 slidably supported within the housing 509 to apply a force to the container 530 so as to move the container 530 towards the nozzle 511 and actuate the compression pump.

The lever 520 has two flanges each of which is slidably supported by means of rails 555, 556 that are engaged with U-shaped guides 557 formed in the housing 509.

A pre-load means is provided to prevent the pump being actuated before a pre-determined force is applied to the lever 520.

The pre-load means comprises of a spring 558 interposed between the lever 520 and the container 530 and a latching means 560, 561. The spring 558 is used to urge the container 530 towards the nozzle 511 so as to actuate the compression pump.

The spring is interposed between a collar 540 connected to the container 530 and a base plate 541. A transfer rod 542 extends out from each side of the base plate for engagement with an inclined surface 543 formed on each flange of the lever 520. When the lever 520 is pushed or urged by a user towards the container 530 the transfer rods 542 move up the inclined surfaces 543 thereby compressing the spring 558. However, the container 530 is not moved because the collar 540 is connected to the housing 509 by the latching means 560, 561.

The latching means comprises of a rib 560 formed on an internal wall of the housing 509 and two outwardly extending arm 561 connected to the collar 540.

Each of the arms 561 is connected to the collar via a living hinge 563 so that when the collar 540 moves towards the nozzle 511 the arms 561 are able to abut against the collar 540 and so transfer load to the rib 560 but when the collar 540 is moving away from the nozzle 511 the arms 561 are able to flip up so as to allow them to pass freely over the rib 560. A return spring 565 is provided to return the lever 520 to its normal rest position when no force is being applied to it.

Operation of the fluid dispensing device is as follows.

The application of an initial force to the lever 520 causes the spring 558 to be compressed by the movement of the lever 520 without any movement of the container 530 occurring due to the engagement of the arms 561 with the rib 560. This will continue until a pre-determined force is applied, at which point the means used to prevent actuation of the compression pump, that is to say the arms 561 and the rib 560, are overcome by the force being applied to the container 530 by the spring 558 and the container 530 moves rapidly towards the nozzle 511 so as to actuate the compression pump.

Upon releasing the force from the lever 520 it is returned to its rest position by the return spring 565 and a spring within the pump returns the container back to its rest position so that the arms 561 re-engage with the rib 560.

The use of a spring to move the container has the advantage that a known force is used to move the container and so a consistent spray can be produced.

With reference to FIGS. 25 to 29 there is shown a further embodiment of a fluid dispensing device 605 for spraying a fluid into a body cavity comprising a body structure including a housing 609, a nozzle 611 extending out from an upper end of the housing for insertion into a body cavity, a fluid discharge device 608 moveably housed within the housing 609, the fluid discharge device 608 comprising a container 630 having a neck 629 at one end for storing the fluid to be dispensed and a compression pump having a suction inlet located within the container 630 and a discharge outlet 631 for transferring fluid from the pump to the nozzle 611 and at least one lever 620, 621 to apply a force to an actuating means 622 used to move the container 630 towards the nozzle 611 so as to actuate the pump. The two opposing levers 620, 621 are pivotally supported at a lower end within the housing 609 and the actuating means 622 is connected to the neck 629 of the container 630 by a collar 640 engaged with the neck 629 of the container 630.

The collar 640 can be attached or engaged with the neck 629 by any suitable means but preferably the collar 640 is designed to snap onto the neck 629 and locate in a groove formed in the neck 629. This arrangement using a snap-on collar allows a standard fluid discharge device to be used without modification.

The fluid dispensing device 605 comprises of a plastic moulded body 606 and the fluid discharge device 608 and further comprises of a protective end cap (not shown) having an inner surface for engagement with the body 606 to protect the dispensing nozzle 611.

The body 606 is made from a plastic material such as polypropylene and the body 606 and the nozzle 611 are made as a single plastic component and are connected to an upper end of the housing 609 so that the nozzle 611 extends away from the housing 609.

The housing 609 defines a cavity formed by a front wall, a rear wall and first and second end walls 614a, 614b. Each of the side walls 614a, 614b has an aperture 618a, 618b formed therein through which the upper end of a restive one of the levers 620, 621 projects.

At least one of the front wall and the rear wall has an aperture (not shown) therein to view the level of the fluid in the container 630.

The discharge outlet from the pump is in the form of a tubular delivery tube 631 and a tubular guide in the form of an outlet tube 616 is formed within the nozzle 611 to align and locate the delivery tube 631 correctly with respect to the nozzle 611.

An annular abutment 617 is formed at the end of the outlet tube 616. The annular abutment 617 defines the entry to an orifice passage 615 through which fluid can flow in use and is arranged for abutment with an end of the delivery tube 631.

The nozzle 611 and the fluid discharge device both have longitudinal axes which are aligned so that when the pump is actuated the force applied to the tubular delivery tube 631 is along the axis of the tubular delivery tube and no bending or deflection of the delivery tube 631 will occur due to the applied force.

The fluid discharge device 608 is in most respects conventional and will only be described briefly herein.

The fluid discharge device 608 comprises of the hollow container 630 defining a reservoir containing several doses of the fluid to be dispensed and the compression pump attached to said one end of the container 630.

The container 630 as shown is made from a translucent or transparent plastics material however it will be appreciate that it could be made from other translucent or transparent materials such as glass.

The pump includes a plunger (not shown) slidingly engaged within a pump casing that defines a chamber (not shown) sized to accommodate a single dose of fluid. The plunger is attached to the tubular delivery tube 631 that is arranged to extend from one end of the pump for co-operation with the outlet tube 616 of the dispensing nozzle 611. The plunger includes a piston (not shown) slidably supported in the chamber formed in the pump casing.

The fluid is discharged through a discharge channel defined by the tubular delivery tube 631 into the orifice passage 615 of the dispensing nozzle 611.

The size of chamber is such that it accommodates a single dose of fluid, the diameter of the chamber and piston combined with the stroke of the plunger being such that a full stroke of the plunger in the chamber will produce a change in volume equal to a single dose of fluid.

The pump casing is connected to the container 630 such that when the piston is moved by a return spring (not shown) into a start position a new dose of fluid is drawn into the cylinder via the suction inlet in the form of a pick-up tube from the container 630 ready for discharge.

The two opposing levers 620, 621 are each pivotally supported near a lower end of the housing 609 by means of pivot pins 623 which pivotally connect each lever 620, 621 to part of the housing 609. The two levers 620, 621 are arranged to act upon the actuating means 624 so as to urge the container 630 towards the nozzle 611 when the two levers 620, 621 are squeezed together by a user. It will be noted that the levers 620, 621 are relatively elongate to enable mechanical advantage to be provided in use.

The actuating means comprises of at least one elongate member 624 interposed between a position of connection 'PC' to the collar 640 and a position of interaction 'PI' with a respective lever 620, 621.

The position of interaction 'PI' is a position where an end portion of each elongate member 624 reacts against a stop 625 associated with the respective lever 620, 621.

The stop is in the form of a projection or rib 625 on a surface of the respective lever 620, 621 facing the container 630. The projection 625 is formed as an integral part of the respective lever 620, 621 by being moulded as a part of the lever 620, 621.

Alternatively, the stop could be formed by a component attached to the lever or could be a recess formed in a surface of the respective lever facing the container with which the end portion of the elongate member may be engaged.

In any event the stop 625 is arranged to prevent sliding of the elongate members 624 beyond a certain position along the length of each lever 620, 621 and are used to transfer load from each lever 620, 621 to the elongate members 624.

Figure 25:
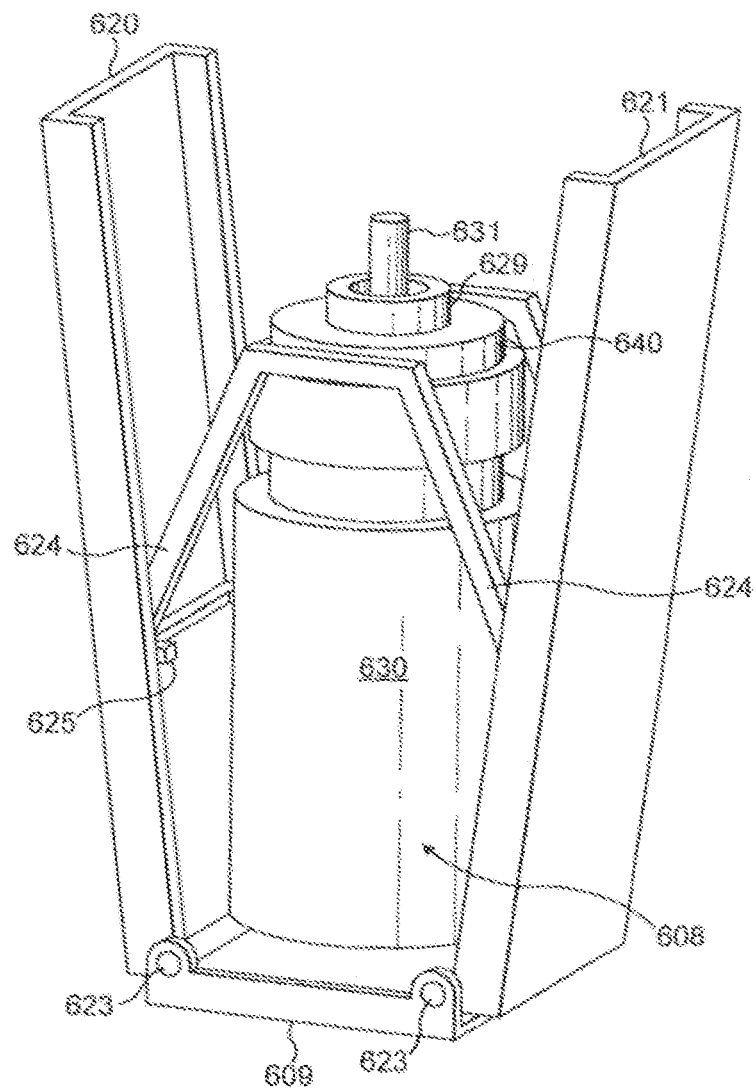
FIG. 25 is a pictorial representation of part of a further fluid dispensing device according to the invention in a ready for use state.

The elongate members 624 are formed as an integral part of the collar 640 and as shown in FIG. 25 there are two elongate members 624 interposed between each lever 620, 621 and the collar 640.

Figure 26:
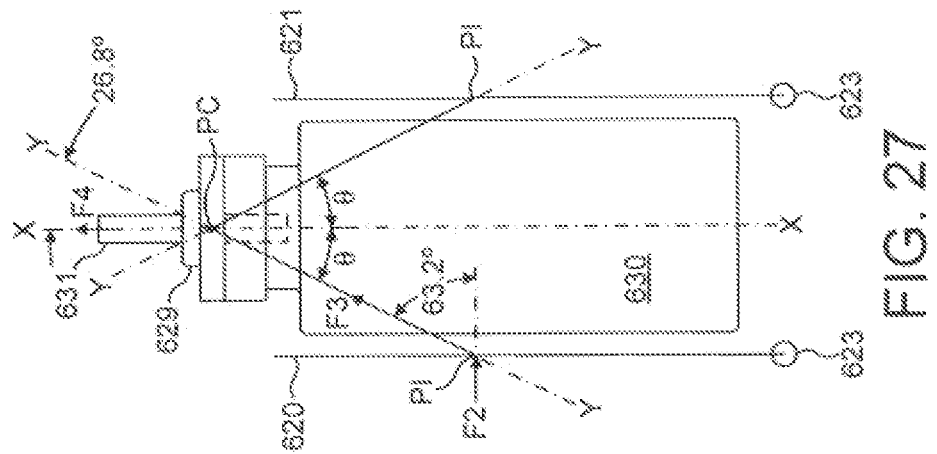
FIG. 26 is a line diagram showing the relationship between various members forming the fluid dispensing device in a ready to use position.
Figure 27:
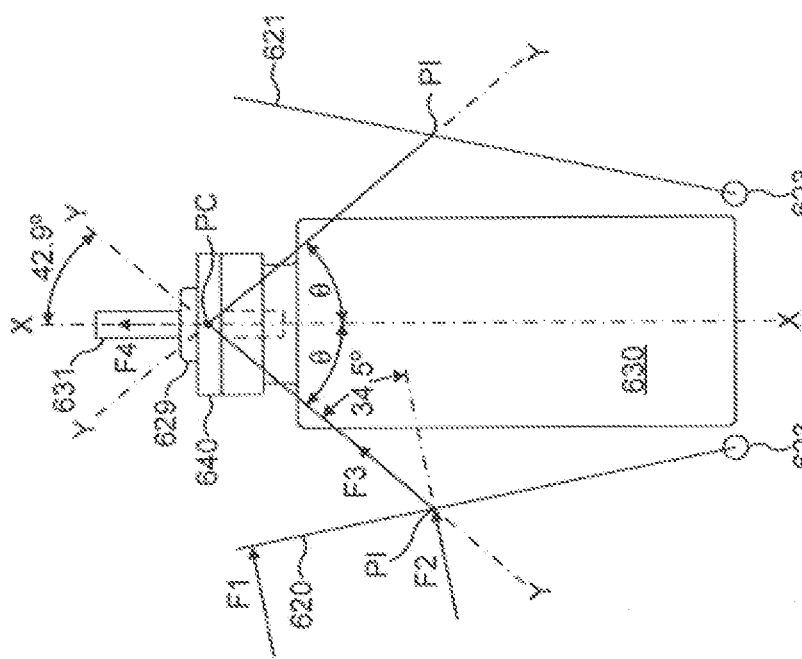
FIG. 27 is a line diagram similar to that shown in FIG. 26 but showing the position of the members in a discharged state at the end of a delivery stroke.

As is best understood with reference to FIGS. 26 and 27 the container 630 has a longitudinal axis X-X and each elongate member 624 has a longitudinal axis Y-Y extending between the position of connection 'PC' to the collar 640 and the position of interaction 'PI' with the respective lever 620, 621. The longitudinal axis Y-Y of each elongate member 624 is arranged at an included angle θ with respect to the longitudinal axis X-X of the container 630 such that the respective elongate member 624 diverges away from the longitudinal axis X-X of the container as it extends from the position of connection 'PC' to the collar 640 to the position of interaction 'PI' with the respective lever 620, 621.

When the or each lever 620, 621 is moved to cause the container 630 to be moved towards the nozzle 611, the included angle θ between the longitudinal axis Y-Y of each elongate member 624 and the longitudinal axis X-X of the container 630 is reduced as is shown in FIG. 27. This is because when each lever 620, 621 is moved to cause the container 630 to be moved towards the nozzle 611, each elongate member 624 associated therewith is subjected to elastic bending. That is to say the elongate members are bent but when the applied load is released they return to their normal straight condition.

Figure 28:
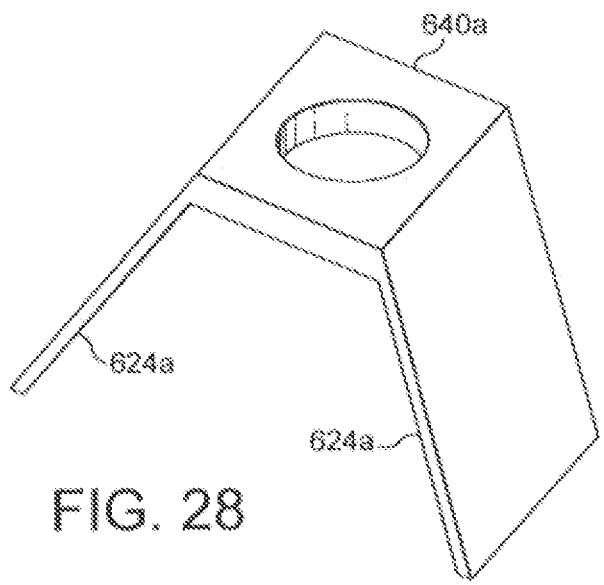
FIG. 28 is a pictorial representation of an alternative collar and actuating means for use in the fluid dispensing device shown in FIG. 25.

FIG. 28 shows an alternative form of collar 640*a* and elongate members 624*a* in which each of the elongate members 624*a* is formed by a strip or leaf of resilient flexible material. The collar 640*a* and the elongate members 624*a* are formed as a single integral part.

Referring to FIG. 26 if a force F1 is applied to the lever 620 where shown then this will result in a force F2 being transferred to the end of the two elongate members 624 from the project 625. Because of the angle at which the elongate members 624 are positioned the two elongate members 624 transmit a force F3 to the collar 640 and once again because of the angle at which this force is applied the force F3 results in a force F4 being transmitted along the axis X-X of the container 630 to move the container in the direction of the nozzle so as to actuate the pump.

Given the angles and geometry shown on FIG. 26 an input force F1 of 20 Newton will result in an ultimate output force F4 of 29.3 Newton.

However, due to the change in the angles which occurs as the levers 620, 621 are squeezed together, the same input force F1 of 20N will result in an ultimate output force F4 of 65.3N being applied to the container 630 at the end of the delivery stroke as shown in FIG. 27.

The material of construction of elongate members 624; 624*a* is selected such that flexing occurs only after a certain minimum input (i.e. threshold) force is employed. Once this threshold force is exceeded flexing of the elongate members 624; 624*a* occurs readily.

This increase in mechanical ratio is useful as it ensures that when a user applies a force to the levers 620, 621 a positive movement of the container occurs resulting in a short but powerful spraying action.

Operation of the fluid dispensing device is as follows.

Figure 29:
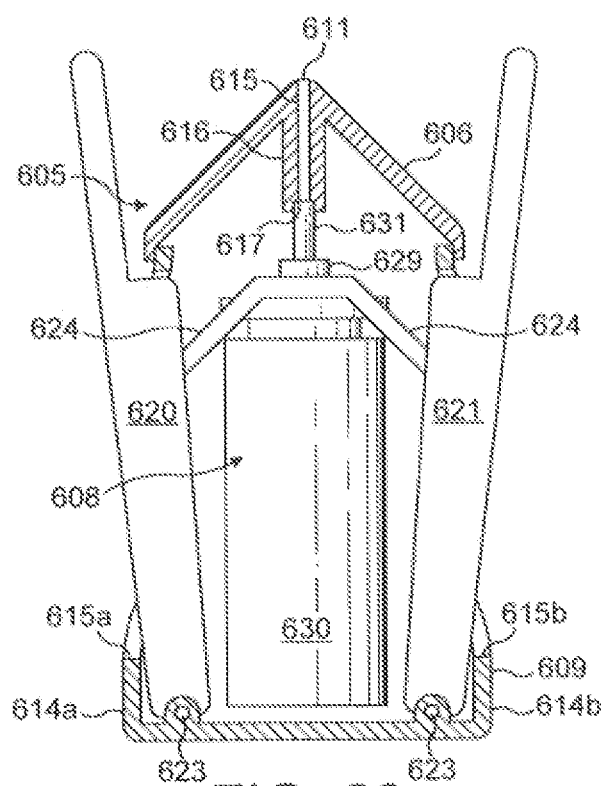
FIG. 29 is a cross-section through a fluid dispensing device of which the mechanism shown in FIG. 25 forms a part.

FIG. 29 shows the levers 620, 621 in a ready for use position in which the levers 620, 621 are used to hold the fluid discharge device 608 within the housing 609. In this position the end portions of the elongate members 624 rest upon the stops 625.

If required, the container 630 could additionally be slidably engageable with one or more support structures (not shown) to assist with the location and retention of the fluid discharge device 608 in the housing 609.

If a user then grasps the fluid dispensing device 605 by the two levers 620, 621 then provided only a light pressure is applied to the levers 620, 621 no fluid will be discharged and the user is able to manoeuvre the dispensing nozzle 611 of the fluid dispensing device 605 into the body orifice into which fluid is required to be dispensed. This is because of the presence of static friction between the pivot pins 623 and the levers 620, 621 and also because the selected material of construction for the elongate member 624 does not allow flexing until a minimum threshold force is applied.

If the user then squeezes the two levers 620, 621 together with increasing force the threshold force will be overcome and the interaction of the flexing elongate members 624 with the projections 625 will then cause a force to be transmitted to the collar 640 and the container 630 will be moved rapidly towards the nozzle 611. During this part of the operation the elongate members are subject to elastic bending as the rotational movement of the levers 620, 621 causes the projections 625 on each lever 620, 621 to be moved closer together.

Because of the abutment between the end of the delivery tube 631 and the annular abutment 617, movement of the delivery tube 631 in the same direction is not possible. The effect of this is to cause the container 630 to move relative to the delivery tube 631 causing the delivery tube 631 to push the plunger into the pump casing thereby moving the piston of the pump in the cylinder. This causes fluid to be expelled from the cylinder into the delivery tube 631.

The fluid forced into the delivery tube 616 is then transferred into the orifice 615 from where it is expelled as a fine spray into the body orifice.

Upon releasing the pressure applied to the levers 620, 621 the delivery tube 631 is urged out of the pump casing by the internal return spring and by the natural reaction of the elongate members to return to a straight form and causes fluid to be drawn up the pick-up tube to re-fill the cylinder.

The actuating procedure can then be repeated until all of the fluid in the container has been used. However, only one or two doses of fluid are normally administered at a time.

When the container is empty a new fluid discharge device 608 is loaded into the housing 609 thereby restoring the fluid dispensing device 605 into a useable condition.

FIGS. 30 to 40 show another fluid dispensing device 705 suitable for spraying a fluid into a nasal cavity of a human user which is in accordance with the present invention.

The fluid dispensing device 705 comprises a plastics housing 709 (e.g. of ABS), a nozzle 711 for insertion into the nasal cavity at an upper end of the housing 709 and a fluid discharge device 708 housed within the housing 709 for reciprocal translation along its longitudinal axis X-X. As shown in FIGS. 30 to 34, when the fluid discharge device 708 is received in the housing 709, its longitudinal axis X-X is in-line with the nozzle 711.

The outer surface, or a part of the outer surface, of the nozzle 711 can be made from a soft-touch plastics material. However, in this embodiment the nozzle 711 is made from polypropylene (PP).

The fluid discharge device 708 comprises a container 730, for storing enough of the fluid for multiple metered doses thereof to be dispensed, and a compression pump 729 mounted on the container 730. The container 730 is made from a translucent or transparent plastics material, although it will be apparent that it could be made from other translucent or transparent materials, such as glass. The pump 729 has a suction inlet 761, in the form of a dip tube, located within the container 730 and a discharge outlet 763, in the form of a pump stem, for transferring fluid from the pump 729 to the nozzle 711.

The housing 709 is provided with a window 750 through which the level of the fluid in the container 730 can be checked.

Pivotally mounted to the housing is a finger operable means 720 to apply a force to the container 730 in a direction which is transverse to the longitudinal axis X-X. This transverse force moves the container 730 towards the nozzle 711 along the longitudinal axis X-X so as to actuate the pump 729. The finger operable means is in the form of a lever 720 (e.g. of ABS) pivotally connected at its lower end to the housing 709 and arranged to act upon the container 730 so as to urge the container 730 towards the nozzle 711 when the lever 720 is pivoted inwardly by a user's finger or thumb.

A protective end cap 707 is provided for protection of the nozzle 711. First and second lugs 749a, 749b project from the protective end cap 707 for receipt within suitably arranged channels 751a, 751b provided within the housing 709 such as to allow secure attachment of the end cap 707 to the housing 709. When so-received, first lug 749a further interferes with movement of lever 720 such as to prevent actuation (i.e. to lock movement) of the lever 720 when the end cap 707 and lugs 749a, 749b are in place (i.e. in the nozzle covered position).

The end cap 707 also has a protruding stopper 760 which has a convex, resilient end form 761 arranged for sealing engagement with the dispensing orifice 715 of the nozzle 711 so as provide an essentially airtight seal to nozzle orifice 715 to prevent fluid drain back when the stopper 760 is in place.

The end cap is suitably made from the same material as the housing, e.g. a plastics material, suitably ABS.

Figure 36A:
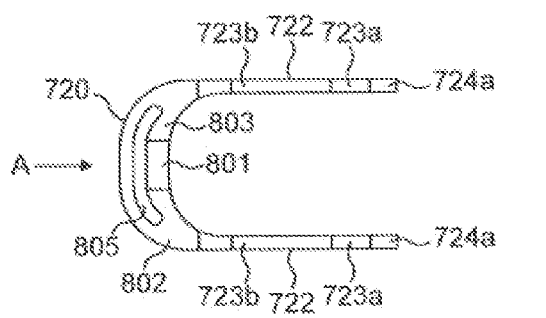
FIG. 36A is a schematic plan view of an actuator lever of the fluid dispensing device of FIG. 30.

As will be understood by reference to FIGS. 32, 34 and 36A, the lever 720 has a pair of beaks or noses 721 which each present a cam surface 722 arranged for interaction with one of a pair of cam follower surfaces 792 provided on a collar 790 (e.g. of acetal) fixed around the neck of the container 730. It will be appreciated that a sideways force (i.e. substantially transversely to the longitudinal axis X-X of the fluid discharge device 708) applied to the lever 720 results in the cam follower surfaces 792 riding over the cam surfaces 722 thereby resulting in upward movement (i.e. along the longitudinal axis X-X) of the fluid discharge device 708.

In more detail, the beaks 721 are located at the upper end of the lever 720 on opposite sides thereof. In plan view, the upper end of the lever 720 has a U-shaped cross section, as shown in FIG. 36A. The beaks 721 straddle opposed sides of the fluid discharge device 708 for co-operation with the diametrically opposed cam follower surfaces 792 on the collar 790. Noting that the fluid dispensing device 705 only has one actuator lever 720, the use of a pair of beaks 721 improves the ability of the lever 720 to cam the fluid discharge device 708 upwardly along its longitudinal axis X-X.

Each cam surface 722 of the lever 720 has a variable mechanical ratio arranged such that until a pre-determined force is applied to the lever 720 no significant force is transferred to the container 730. In more detail, each cam surface 722 has a commitment portion 723a which is inclined at a first angle to the longitudinal axis X-X of the fluid discharge device 708 and a drive portion 723b inclined to the longitudinal axis X-X at a second angle which is greater than the first angle. The first angle should be no less than approximately 20°, and is suitably in the range of approximately 20-35°, more suitably approx. 20-26°, even more suitably approx. 22-26°. The second angle may be in the range of approximately 40-60°, suitably approx. 40-50°, more suitably approx. 45°.

Therefore, when an inward force is initially applied to the lever 720 it is applied substantially normally to the longitudinal axis X-X of the fluid discharge device 708 and virtually no force is converted into a force along the longitudinal axis X-X of the fluid discharge device 708 and so the static friction between the commitment portions 723a of the beaks 721 and the cam follower surfaces 792 is sufficient to maintain the lever 720 effectively stationary. However, when a pre-determined load is applied to the lever 720 the static friction is overcome and the cam follower surfaces 792 start riding on the commitment portions 723a.

When the cam follower surfaces 792 reach the end of the commitment portions 723a, the increase in inclination of the cam surfaces to the longitudinal axis X-X in combination with the magnitude of the force being applied ensures that the cam follower surfaces 790 suddenly slide rapidly along the drive portions 723b causing the container 730 to be moved rapidly towards the nozzle 711 to actuate the compression pump. This ensures that the pump is only actuated when sufficient force is being applied to produce an effective spray from the nozzle 711.

Figure 39:
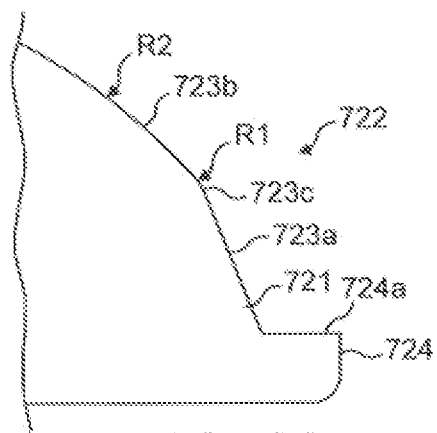
FIG. 39 is an enlarged view of one of a pair of beaks of the lever of FIG. 36A which present a cam profile.

Referring to FIG. 39, it will be seen that the commitment portions 723a are planar sections of the cam surfaces 722, whereas the drive portions 723b are arcuate. More specifically, the drive portions 723b have a short rounded transition section 723c contiguous with the associated commitment portion 723a. The transition sections 723c have a radius of curvature R1 which is greater than the radius of curvature R2 of the remainder of the drive portion 723b, which radius R2 is constant over the length of the remainder of the drive portion 723b. The transition portions 723c smooth the transfer of the cam follower surfaces 729 from the commitment portions 723a of the cam surfaces 722 to the drive portions 723b. They also reduce wearing of the cam surfaces 722.

R1 in this embodiment is about 3 mm, while R2 is about 25 mm. Nonetheless, other radii could be used, as will be appreciated by the skilled person in the art.

Referring to FIG. 32, the cam follower surfaces 792 are rounded edges of diametrically-opposed embossments 793 on the plastic collar 790. This makes riding of the cam follower surfaces 792 on the cam surfaces 722 easier, and also reduces wearing of the respective surfaces.

As shown in FIGS. 34 and 39, the beaks 721 have a tip which forms a cradle 724 for the embossments 793 on the collar 790 of the fluid discharge device 708 to rest on. The cradles 724 present a support surface 724a which extends transversely to the longitudinal axis X-X on which the embossments 793 can be supported. The cradles 724 act as a back-stop for the fluid discharge device 708 insofar as preventing the fluid discharge device 708 moving downwardly beyond the point at which the cradles 724 engage with the embossments 793. As will be seen from FIG. 34, this ensures that the cam follower surfaces 792 are aligned with the commitment portion 723a of the cam surfaces 722.

Noting that the lever 720 pivots inwardly, it will be appreciated that as the lever 720 pivots inwardly the inclined angle which the planar commitment portions 723a make with the longitudinal axis X-X becomes smaller (steeper) thereby increasing the resistance of the fluid discharge device 708 to being cammed upwardly.

However, the arcuate nature of the drive portions 723b, in particular that part after the transition section 723c, is such that the inclined angle it makes with the longitudinal axis X-X remains the same, or substantially the same, as the lever 720 pivots inwardly. More specifically, consider that as the lever 720 pivots inwardly the point on the section of the drive portion 723b having the radius of curvature R2 which is in contact with the cam follower surface 792 moves up the cam surface 722. The angle that a tangent to this changing contact point makes with the longitudinal axis X-X remains the same, or substantially the same, as the lever 720 pivots inwardly to cause the fluid discharge device 708 to spray a metered dose of the fluid product from the nozzle 711. This feature means that the resistance to the inward movement of the lever 720 never increases after the commitment feature has been overcome, as would be the case if the drive portion 723b were a planar surface since its angle to the longitudinal axis X-X would then increase as the lever 720 pivots inwardly.

The aforementioned features of the cam profile mean that the operator receives smooth tactile feedback from the device 705 when the lever 720 is actuated to cause the fluid discharge device 708 to spray a metered dose of the fluid product from the nozzle 711.

To use the fluid dispensing device 705 a user first has to remove the protective cap 707 thereby unsealing the nozzle orifice 715 by removing the stopper end 760 therefrom. The user then grasps the fluid dispensing device 705 and places a thumb and/or finger on the lever 720.

Provided that only a light pressure is applied to the lever 720 no fluid will be discharged and the user is able to manoeuvre the dispensing nozzle 711 of the fluid dispensing device 705 into one of their nostrils so that the fluid is able to be dispensed into the nasal cavity.

If the user then squeezes the lever 720 inwards with increasing force the threshold force defined by the interaction of the cam follower surfaces 792 with the commitment portions 723a of the cam surfaces 722 is overcome resulting in the container 730 being moved rapidly towards the nozzle 711 to actuate the pump 729 and dispense fluid to the dispensing orifice 715. Upon release of the pressure applied to the lever 720 the pump is reset by its internal return spring. Moreover, the lever 720 has a leaf spring 765 (FIG. 30) which acts against a housing inner wall 767 to bias the lever 720 to its rest position shown in FIGS. 29 to 32 and 34.

The actuating procedure can then be repeated until all of the fluid in the container 730 has been used. However, only one or two doses of fluid are normally administered at a time.

Figure 38:
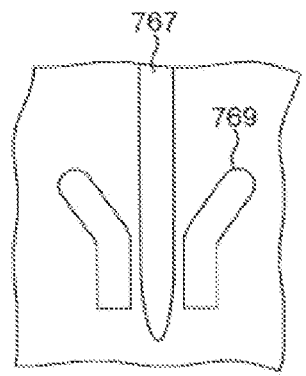
FIG. 38 is a schematic representation of a guide mechanism of the fluid dispensing device of FIG. 30.

Referring to FIGS. 34 and 38, to counteract the lateral force which the lever 720 applies to the fluid discharge device 708, and to guide the axial displacement of the fluid discharge device 708 in response to the lever operation, the collar 790 has a pair of diametrically opposed tracks 769 which are arranged parallel to the longitudinal axis X-X. These tracks 769 are provided by the embossments 793. Each track 769 has a funnel shape at its upper end for self-guiding of the tracks 769 onto complementary axially-extending runners 767, presented on the inner surface of the housing 709, when the fluid discharge device 708 is inserted into the housing 709 through an (lower) opening 771 in its lower end, which lower opening 771 is subsequently closed with a cap 772. It will also be appreciated that the track-runner mechanism positions the collar 790 in the correct angular orientation about the longitudinal axis X-X so that the cam follower surfaces 792 face the cam surfaces 722.

In use, the tracks 769 ride on the runners 767 when the lever 720 overcomes the threshold force provided by the commitment portions 723a of the cam surfaces 722. As will be appreciated, the co-operation of the tracks 769 with the runners 767 prevents rotation of the collar 790 in the housing 709.

Figure 30:
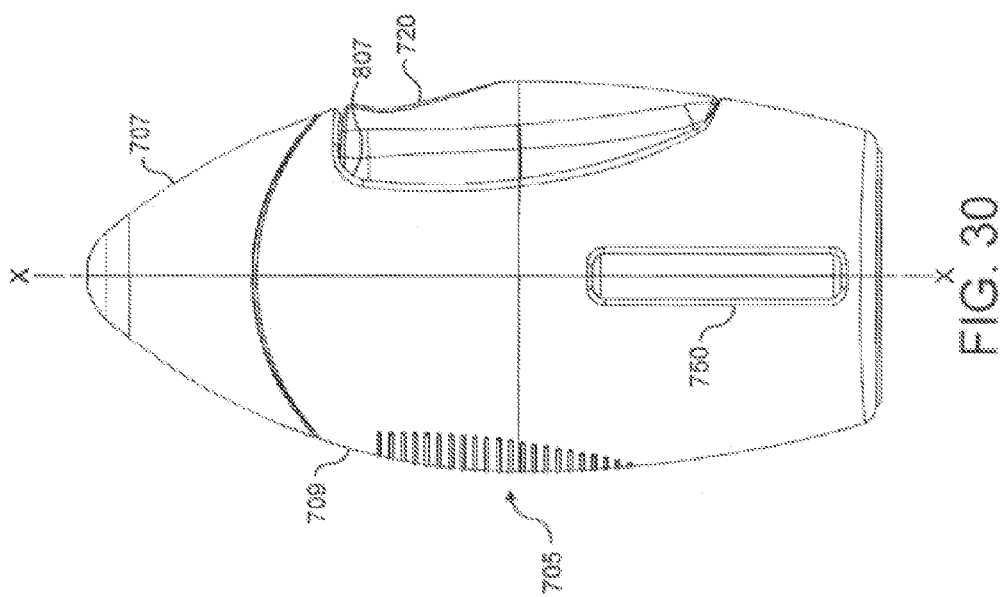
FIG. 30 is a side view of another fluid dispensing device of the invention.

In addition to the tracks 769, the collar also has a sheath 773 for the pump stem 763 which forms a sliding fit on an inner hollow post 775 of the nozzle 711 in which a nozzle outlet passage 777 is formed. As shown in FIG. 30, the pump stem 763 is located in a lower widened portion of the outlet passageway 777 through an interference fit. It will therefore be appreciated that the pump stem 763 remains stationary in the housing 709 as the container 730 and the collar 790 are translated upwardly by the lever 720, i.e. there is relative movement between the container-collar unit and the pump stem. In this way, the pump 729 is compressed and a metered dose of the fluid product discharged through the pump stem 763 into the outlet passageway 777 for ejection from the nozzle orifice 715 at the end of the outlet passageway 777. The commitment feature on the lever 720 ensures that the pumping force is sufficient for atomisation of the fluid product from the nozzle 711.

Figure 37:
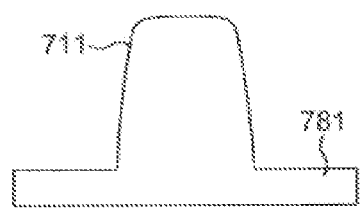
FIG. 37 is a side view of the nozzle of FIG. 35.

As shown in FIG. 37, the nozzle 711 in this embodiment is formed as a separate part from the housing 709. This has advantages when the fluid product being dispensed is a medicament because this isolates the only part of the device that comes into contact with the medicament. Accordingly, testing of the pharmaceutical performance of the nozzle 711 can be conducted without the need for the housing 709. So, once the nozzle 711 is complete, testing of it can begin while the development and design of the housing 709 continues. Therefore there is no hold up in the device development, as would be the case if the nozzle 711 were integrally formed with the housing 709. Any change in the moulding of the housing would require re-testing of the nozzle 711 to confirm that the new moulding has had no adverse effect on the nozzle performance.

In addition, having a separate nozzle 711 means that the housing 709 can be customised for different markets and/or different products. As an example, the nozzle 711 could be a universal nozzle for a set of housings having different shapes, different colours, etc.

A further advantage of a separate nozzle 711 is that it can be more easily formed from a different material than the housing 709, for example one that is more acceptable for insertion into a nostril and/or for contacting the fluid product, especially where this is a medicament, but which might be too expensive to form the whole housing 709 from.

To this end, and as shown in FIG. 30, the housing 709 has an (upper) opening 780 at its upper end through which the nozzle 711 is insertable.

Figure 31:
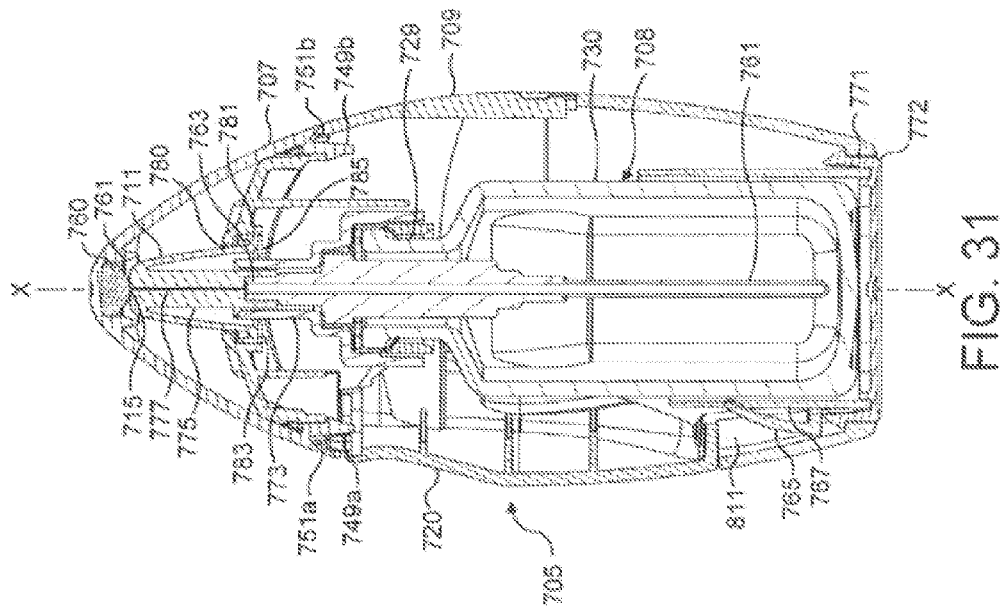
FIG. 31 is a longitudinal sectional view of the fluid dispensing device of FIG. 30.
Figure 35:
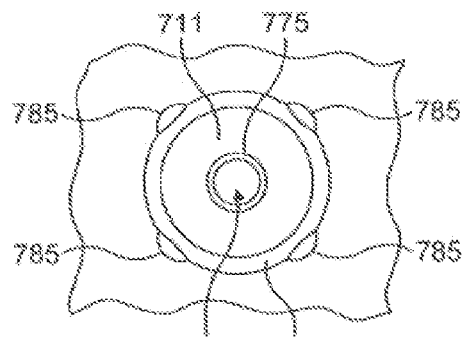
FIG. 35 is a fragmentary, enlarged underneath plan view of a nozzle of the fluid dispensing device of FIG. 30 mounted in a housing of the device.

Referring to FIGS. 31, 35 and 37, the nozzle 711 has a flange 781 at its lower end which engages the inner mouth of the upper opening 780 so that the tip of the nozzle 711 projects from the upper opening 780 the required distance for nasal use. As will be seen from FIGS. 31 and 35, the inner mouth of the upper opening 780 is bounded by a collar 783 formed from a series of collar segments 785 angularly spaced-apart about the longitudinal axis X-X. The collar segments 785 are bent over the nozzle flange 781 by a swaging tool to clamp the nozzle flange 781 against the inner mouth to fix the nozzle 711 in the upper opening 780.

To assist in assembly of the fluid dispensing device 705, the lever 720 is provided with means to enable it to be disposed in an outward position with respect to the housing 709, to allow the fluid discharge device 708 to be inserted into the housing 709 through the lower opening 771 to its rest position shown in FIGS. 30, 32 and 34, and the inward position with respect to the housing 709 shown in FIGS. 30 to 32.

Figure 36B:
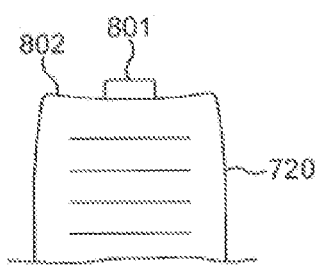
FIG. 36B is a side view of the lever taken on arrow A in FIG. 36A.
Figure 40:
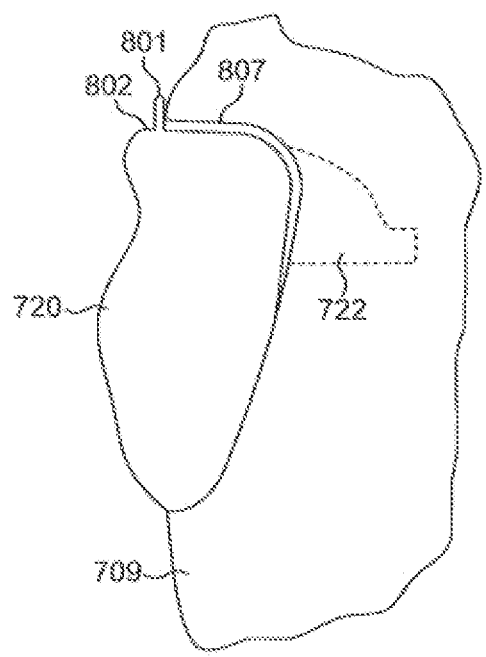
FIG. 40 is a fragmentary, schematic view of the lever of FIG. 36A in an outward position relative to the housing of the fluid dispensing device of FIG. 30.

Referring to FIGS. 36A, 36B and 40, at the upper end of the lever 720 there is provided a tab 801 which projects above the upper edge 802 of the lever 720. The tab 801 projects from a resilient bridge element 803 formed by a cut-out 805 in the lever 720. The resilient bridge element 803 biases the tab 801 to its extended position shown in FIGS. 36A, 36B and 40, but enables the tab 801 to be depressed so that it is flush with, or below, the lever upper edge 802.

As will be understood from FIG. 30, the lever 720 is mounted in a slot 807 formed in the side of the housing 709. The lever 720, which is formed separately from the housing 709, but from the same plastics material, is mounted to the housing by first inserting its lower end 809, which carries the leaf spring 765, through the slot 807 to be received in an axial channel 811. The lever 720 is now disposed in its outward position with the tab 801 bearing against the edge of the slot 807 to prevent the lever 720 being moved through the slot 807 to its inward position, as schematically shown in FIG. 40.

When the lever 720 is in its outward position, the fluid discharge device 708 is able to be inserted into the housing 709 through the lower housing opening 771 to its rest position because the lever 720, and its beaks 722 in particular, do not impede the loading of the fluid discharge device 708.

After the fluid discharge device 708 has been loaded to its rest position, the lever 720 is moved to its inward position by depressing the tab 801 so that it clears the edge of the slot 707 and then pushing the lever 720 inwardly to its position shown in FIG. 31, for example. If the lever 720 were in its inward position before the fluid discharge device 708 were loaded into the housing 709, the fluid discharge device could not be loaded into the housing 709 to its rest position, not without damaging the lever 720 in any event.

As shown in FIG. 31, for example, once the lever 720 is moved to its inward position, the tab 801 returns to its extended position and bears against an inner surface of the housing 709 to maintain the lever 720 in the inward position. In this regard, the lever leaf spring 765 biases the lever 720 outwardly.

In more detail, the tab 801 bears against an inner surface of one of the channels 751a in the housing 709 in which the cap lugs 749a, 749b are snap-fitted to hold the protective cap 707 releasably captive on the housing 709. As shown in FIG. 31, the lug 749a received in the channel 751a is located in front of the tab 801. It will therefore be gathered that the lever 720 is prevented from moving inwardly when the cap 707 is in place, to actuate the fluid dispensing device 705, by the lug 749a blocking inward movement of the lever tab 801.

Those parts of the fluid dispensing device 705 made from a plastics material are formed by a moulding process.

In accord with the present invention, the container 30, 130, 230, 330, 430, 530, 630, 730 of the fluid dispensing devices of FIGS. 1 to 40 contains a fluid medicament formulation having a viscosity of from 10 to 2000 mPa·s at 25° C.

The fluid medicament formulation is in one aspect, formulated as a solution formulation. In another aspect, the fluid medicament formulation is formulated as a suspension formulation comprising a suspension of active medicament particles in an inert suspending formulation.

Suspension Formulation

A suitable suspension formulation for containment by the container herein has the following formulation:

| | |
|---|---|
| Particulate medicament (MMD 3 μm) | 0.05-0.1% w/w |
| Polysorbate 80 | 0.025% w/w |
| Avicel RC591 | 1.5% w/w |
| Dextrose | 5.0% w/w |
| BKC | 0.015% w/w |
| EDTA | 0.015% w/w |
| Water | to 100% |

The particulate medicament is suitably either fluticasone propionate or 6α,9α-Difluoro-17α-[(2-furanylcarbonyl)oxy]-11β-hydroxy-16α-methyl-3-oxo-androsta-1,4-diene-17β-carbothioic acid S-fluoromethyl ester.

The viscosity of the above suspension formulation is about 25 mPa·s.

The suspension formulation was prepared following the following protocol:

Part A
1. Dissolve dextrose in purified water
2. Dissolve EDTA in dextrose solution
3. Add Avicel RC591 while stirring
4. Allow suspension to hydrate Part B (separately)
1. Dissolve Polysorbate 80 in purified water at 50-60° C.
2. Prepare slurry of drug in Polysorbate 80 solution Part C
1. Combine suspension of A4 with suspension of B2 and stir
2. Add solution of BKC in purified water and stir
3. Adjust pH with 1N HCl
4. Add purified water to correct weight For use herein, the container 30, 130, 230, 330, 430, 530, 630 of the fluid dispensing devices of FIGS. 1 to 29 is filled with the suspension formulation above in a total amount suitable for 120 actuations. The pre-compression pump of the container is adapted to dispense 50 or 100 μl per actuation, preferably 50 μl.

Solution Formulation

A suitable solution formulation herein has the following formulation:

| | |
|---|---|
| Particulate medicament (MMD 3 μm) | 0.05-0.1% w/w |
| Polyethylene Glycol (PEG 400) | 75% w/w |
| NaCl | 0.9% w/w |
| EDTA Na | 0.015% w/w |
| BKC | 0.015% w/w |
| Water to: | 100% |

The particulate medicament is suitably either fluticasone propionate or 6α,9α-Difluoro-17α-[(2-furanylcarbonyl)oxy]-11β-hydroxy-16α-methyl-3-oxo-androsta-1,4-diene-17β-carbothioic acid S-fluoromethyl ester.

The viscosity of the above solution formulation is >10 mPa·s.

For use herein, the container 30, 130, 230, 330, 430, 530, 630 of the fluid dispensing devices of FIGS. 1 to 29 is filled with the solution formulation above in a total amount suitable for 120 actuations. The pre-compression pump of the container is adapted to dispense 50 or 100 µl per actuation, preferably 50 µl.

It will be appreciated that although the invention has been described with respect to several specific embodiments there are many alternative combinations and arrangements that could be used. The primary objective of the invention is to provide a fluid dispensing device that is operable by one or more finger operable means (e.g. levers) applying a force to a container with respect to a longitudinal axis of the container and which includes some pre-load means to prevent the container from being significantly moved until the force being applied to it reaches a pre-determined threshold magnitude known to produce a reliable high quality spray.

Administration of medicament may be indicated for the treatment of mild, moderate or severe acute or chronic symptoms or for prophylactic treatment. It will be appreciated that the precise dose administered will depend on the age and condition of the patient, the particular medicament used and the frequency of administration and will ultimately be at the discretion of the attendant physician. Embodiments are envisaged in which combinations of medicaments are employed.

The dispensing device herein is suitable for dispensing fluid medicament formulations for the treatment of inflammatory and/or allergic conditions of the nasal passages such as rhinitis e.g. seasonal and perennial rhinitis as well as other local inflammatory conditions such as asthma, COPD and dermatitis.

A suitable dosing regime would be for the patient to inhale slowly through the nose subsequent to the nasal cavity being cleared. During inhalation the formulation would be applied to one nostril while the other is manually compressed. This procedure would then be repeated for the other nostril. Typically, one or two inhalations per nostril would be administered by the above procedure up to three times each day, ideally once daily. Each dose, for example, may deliver 5 µg, 50 µg, 100 µg, 200 µg or 250 µg of active medicament. The precise dosage is either known or readily ascertainable by those skilled in the art.

Viscosity Measurement Test Method

A suitable method for measuring viscosity has the following outline protocol:

Instruments
TA Instruments Advanced Rheometer AR500
TA Instruments Electronic Control Box
Techne Tempette Junior TE-8J Water Bath System
Computer (Compaq Pentium 4)
Material
Standard Acrylic Parallel Plate (60 mm) (Acrylic 5660, 6 cm Flat Plate)
Procedure
The analysis is divided into two parts:
(1) Sample analysis (using the AR Instrument Control Software)
(2) Data analysis (using the TA Data Analysis Software)
Load the AR Instrument Control Software.
Attach the geometry up the drive shaft of the rheometer.
Set temperature to 25° C.
Conduct rotational mapping.
Conduct Zero Gapping.
Load the required Flow Procedure Settings as set out below:
Instrument and Software Settings
Geometry: Standard acrylic parallel plate (60 mm)
Gap 250 micrometers
Flow Procedure Settings
(A) Conditioning Step
   Settings:
      (i) Initial temperature=25 degree Celcius
         (Wait for correct temperature)
      (ii) Perform pre-shear
         Shear stress=20 Pa
         Duration=1 minute
      (iii) Perform Equilibration
         Duration=10 seconds
(B) Continuous Ramp Step 1
   (i) Test type=Continuous ramp
   (ii) Test settings:
      Ramp=Shear stress (Pa) from 0.2358 Pa to 20 Pa
      Duration=1 minute
      Mode=Linear
   (iii) Sampling points=12
   (iv) Other settings:
      Temperature=25 degree Celcius
(C) Post-Experimental Step
   (i) Settings:
      Set temperature=25 degree Celcius
      Auto save results file
(A) Sample Analysis Using the AR Instrument Control Software, test the samples in triplicates following the steps as detailed below.

(i) Invert the sample gently five times to ensure mixing without introducing air bubbles and then load approximate 1.5 ml of sample onto the centre of the Peltier plate.

(ii) Lower down the geometry from the drive shaft to close the gap between the geometry and the Peltier plate down to 250 micrometers. Carefully wipe off excess suspension that smears out from the plate.

(iii) Click 'run' button and then record all the required sample information in the software. Start the analysis.

(iv) At the end of the test run, raise the geometry. Clean the Peltier plate and the geometry using tissue and suitable solvent, typically methanol.

(v) Repeat Step (i) to (iv) with the next test sample.

(B) Data Analysis

Load the TA Data Analysis software.
Load the required results file.
For thixotropic suspensions, conduct analysis of data using Herschel-Bulkley model to fit the flow and viscosity curves.

Type in the required independent values (i.e. shear rate=250 1/sec) and the software will calculate the dependents (i.e. viscosities at 250 1/sec) using the model in addition to indefinite viscosity, yield stress and rate index.

Record the following values as generated by the software.
   (a) Viscosity (indefinite value as derived from the Herschel-Bulkley model)
   (b) Yield Stress
   (c) Rate index
   (d) Viscosity at 250 1/sec
Note:
This protocol is conducted at 25° C.
Note:
Shear stress vs Shear rate profile=Flow curve
Viscosity profile=Viscosity curve The claims of this application may be directed to any feature or combination of features described therein. They may take the form of product, method or use claims and may include, by way of example and without limitation, one or more of the following claims.

What is claimed is:

1. A finger-operable actuating member for a fluid dispensing device for movement transversely with respect to a longitudinal axis of a fluid discharge device of the fluid dispensing device to apply a force to the fluid discharge device to move the fluid discharge device along its longitudinal axis so as to discharge a fluid medicament formulation therefrom, wherein the actuating member comprises:
   a surface for applying the force to a follower of the fluid discharge device,
   wherein the surface has a two-stage profile to provide a pre-load means to prevent discharge from the fluid discharge device until a pre-determined force is applied to the actuating member, and
   wherein the two-stage profile comprises an initial concave high gradient profile and a subsequent convex lower gradient profile such that, in use, no significant force is transferable from the actuating member to the fluid discharge device along the longitudinal axis until the pre-determined force is applied to the actuating member.

2. The actuating member of claim 1, wherein there is a relatively smooth break point between the high and lower gradient profiles.

3. The actuating member of claim 2, wherein the high and lower gradient profiles both have a part-circle form.

4. The actuating member of claim 2, wherein the two-stage profile is disposed at one end of the actuating member.

5. The actuating member of claim 2, wherein the actuating member is a lever.

6. The actuating member of claim 5, wherein the lever is adapted for pivotal movement about a lower end thereof for movement transverse with respect to the longitudinal axis.

7. The actuating member of claim 6, wherein the two-stage profile is disposed at an upper end of the lever.

8. The actuating member of claim 2, in combination with a housing for movably housing the fluid discharge device, wherein the actuating member is comprised in the housing such that the actuating member is movable transversely with respect to the longitudinal axis of the fluid discharge device to apply the force thereto.

9. The actuating member of claim 2, wherein said follower is provided to a container of the fluid discharge device or a fitting on the container.

10. The actuating member of claim 9, wherein the follower is provided to the fitting and wherein the fitting comprises a collar connected to a neck of the container.

11. The actuating member of claim 1, wherein the high and lower gradient profiles both have a part-circle form.

12. The actuating member of claim 1, wherein the two-stage profile is disposed at one end of the actuating member.

13. The actuating member of 1, wherein the actuating member comprises a lever.

14. The actuating member of claim 13, wherein the lever is adapted for pivotal movement about a lower end thereof for movement transverse with respect to the longitudinal axis.

15. The actuating member of claim 14, wherein the two-stage profile is disposed at an upper end of the lever.

16. The actuating member of claim 1, in combination with a housing for movably housing the fluid discharge device, wherein the actuating member is comprised in the housing such that the actuating member is movable transversely with respect to the longitudinal axis of the fluid discharge device to apply the force thereto.

17. The actuating member of claim 1, wherein said follower is provided to a container of the fluid discharge device or a fitting on the container.

18. The actuating member of claim 17, wherein the follower is provided to the fitting and wherein the fitting comprises a collar connected to a neck of the container.

* * * * *